(12) United States Patent
West et al.

(10) Patent No.: US 11,826,446 B2
(45) Date of Patent: Nov. 28, 2023

(54) ORAL CARE COMPOSITIONS COMPRISING PHOSPHONATE AND ANIONIC GROUP CONTAINING POLYMERS

(71) Applicant: The Procter & Gamble Company, Cincinnati, OH (US)

(72) Inventors: Ryan Michael West, West Chester, OH (US); Scott Leroy Cron, Liberty Township, OH (US); Yingkun Jin, Mason, OH (US); William Michael Glandorf, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 17/087,650

(22) Filed: Nov. 3, 2020

(65) Prior Publication Data

US 2021/0052482 A1 Feb. 25, 2021

Related U.S. Application Data

(62) Division of application No. 16/216,329, filed on Dec. 11, 2018, now Pat. No. 11,197,814.

(60) Provisional application No. 62/597,187, filed on Dec. 11, 2017.

(51) Int. Cl.
| | |
|---|---|
| *A61K 8/24* | (2006.01) |
| *A61K 8/46* | (2006.01) |
| *A61Q 11/00* | (2006.01) |
| *A61K 8/81* | (2006.01) |
| *A61Q 1/00* | (2006.01) |
| *A61K 8/21* | (2006.01) |
| *C08F 230/02* | (2006.01) |
| *C08F 228/02* | (2006.01) |
| *C08F 8/12* | (2006.01) |

(52) U.S. Cl.
CPC .............. *A61K 8/24* (2013.01); *A61K 8/21* (2013.01); *A61K 8/466* (2013.01); *A61K 8/817* (2013.01); *A61K 8/8152* (2013.01); *A61K 8/8188* (2013.01); *A61Q 1/00* (2013.01); *C08F 8/12* (2013.01); *C08F 228/02* (2013.01); *C08F 230/02* (2013.01); *A61K 2800/5424* (2013.01); *C08F 2800/10* (2013.01); *C08F 2810/50* (2013.01)

(58) Field of Classification Search
None
See application file for complete search history.

(56) References Cited

U.S. PATENT DOCUMENTS

| | | | |
|---|---|---|---|
| 2,946,725 A | 7/1960 | Norris | |
| 3,070,510 A | 12/1962 | Cooley et al. | |
| 3,678,154 A | 7/1972 | Widder et al. | |
| 3,959,458 A | 5/1976 | Agricola et al. | |
| 3,976,619 A | 8/1976 | Morgan | |
| 4,051,234 A | 9/1977 | Gieske et al. | |
| 4,340,583 A * | 7/1982 | Wason | A61K 8/25 424/57 |
| 4,416,877 A | 11/1983 | Bentzen | |
| 4,420,312 A | 12/1983 | Wason | |
| 4,585,845 A | 4/1986 | Engelhardt | |
| 4,696,987 A | 9/1987 | Duersch | |
| 5,004,597 A | 4/1991 | Majeti et al. | |
| 5,011,913 A | 4/1991 | Benedict | |
| 5,281,410 A | 1/1994 | Lukacovic et al. | |
| 5,575,652 A | 11/1996 | Gaffar et al. | |
| 5,578,293 A | 11/1996 | Prencipe et al. | |
| 5,939,052 A | 8/1999 | White, Jr. et al. | |
| 6,173,049 B1 | 1/2001 | Malik | |
| 6,187,295 B1 | 2/2001 | Glandorf | |
| 6,190,644 B1 | 2/2001 | McClanahan et al. | |
| 6,350,436 B1 | 2/2002 | Glandorf et al. | |
| 6,713,049 B1 | 3/2004 | White, Jr. | |
| 7,399,756 B2 | 7/2008 | Jomaa | |
| 7,871,992 B2 | 1/2011 | Jomaa | |
| 8,017,596 B2 | 9/2011 | Montero | |
| 2003/0165442 A1 | 9/2003 | Baig | |
| 2004/0204541 A1 | 10/2004 | Pelosi | |
| 2005/0063921 A1* | 3/2005 | Charmot | A61Q 11/00 424/48 |
| 2005/0271602 A1 | 12/2005 | Milanovich | |
| 2006/0030546 A1 | 2/2006 | Jomaa | |
| 2006/0241087 A1 | 10/2006 | Montero | |
| 2007/0041914 A1 | 2/2007 | Gaffar et al. | |
| 2008/0249067 A1 | 10/2008 | Jomaa | |
| 2008/0269099 A1 | 10/2008 | Magennis et al. | |
| 2010/0204184 A1 | 8/2010 | Montero | |
| 2011/0112054 A1 | 5/2011 | Jomaa | |

(Continued)

FOREIGN PATENT DOCUMENTS

| | | |
|---|---|---|
| CN | 1993105 A | 7/2007 |
| CN | 102272260 A | 12/2011 |

(Continued)

OTHER PUBLICATIONS

All Office Actions, U.S. Appl. No. 16/215,699.
All Office Actions, U.S. Appl. No. 16/215,702.
All Office Actions, U.S. Appl. No. 16/215,704.
All Office Actions, U.S. Appl. No. 16/216,428.
All Office Actions; U.S. Appl. No. 16/216,039.
All Office Actions; U.S. Appl. No. 16/216,329.
Unpublished U.S. Appl. No. 17/087,650, filed Nov. 3, 2020, to Ryan West et. al.
Unpublished U.S. Appl. No. 17/087,651, filed Nov. 3, 2020, to Ryan West et. al.
Anbar et al. "Organic Polymeric Polyphosphonates as Potential Preventive Agents of Dental Caries: In Vitro Experiments", J Dent Res, vol. 53, No. 4, pp. 867-878, 1974.

(Continued)

*Primary Examiner* — Brian Gulledge
(74) *Attorney, Agent, or Firm* — Elizabeth A. Conklin

(57) ABSTRACT

Disclosed are oral care compositions of phosphonate and sulfonate group containing polymer compositions that have targeted uses with divalent cations and surfaces having divalent cations. These compounds can be used to deliver anionic character to surfaces such as calcium hydroxyapatite.

9 Claims, 1 Drawing Sheet

(56) References Cited

U.S. PATENT DOCUMENTS

| | | | |
|---|---|---|---|
| 2013/0071464 A1* | 3/2013 | Downes | ............... C08F 230/02 526/278 |
| 2016/0324741 A1 | 11/2016 | Baig et al. | |
| 2019/0175485 A1 | 6/2019 | West | |
| 2019/0177348 A1 | 6/2019 | Cron | |
| 2019/0177451 A1 | 6/2019 | West | |
| 2019/0177456 A1 | 6/2019 | West | |
| 2019/0177489 A1 | 6/2019 | West | |
| 2019/0177490 A1 | 6/2019 | West | |

FOREIGN PATENT DOCUMENTS

| | | |
|---|---|---|
| WO | 03009855 A2 | 2/2003 |
| WO | 03050128 A1 | 6/2003 |
| WO | WO2004017334 | 2/2004 |

OTHER PUBLICATIONS

Bingol et al., "Characterization of Oligo(vinyl phosphonate)s by High-Resolution Electrospray Ionization Mass Spectometry: Implications for the Mechanism of Polymerization", Macromolecules 2008, 41, pp. 1634-1639.

Brunet et al., "Engineering of Microcrystaline Solid-State Networks Using Cross-Linked y-Zirconium Phosphate/Hypophosphite with Nonrigid Polyethylenoxadiphosphonates. Easy Access to Porously Dynamic Solids with Polar/Nonpolar Pores", Chem. Mater. 2005, 17, pp. 1424-1433.

Database WPI, Week 200425, Thomson Scientific, London GB, AN 2004-268983, XP002789049.

Frantz et al., "Synthesis and Solid-State NMR Studies of P-Vinylbenzylphosphonic Acid", Chemistry—A European Journal, vol. 9, Issue 3, pp. 770-775, 2003.

Ibrahim Zgani et al. "Synthesis of Prenyl Pyrophosphonates as New Potent Phosphorantigens Inducing Selective Activation of Human V[gamma] 9V[delta] 2 T Lymphocytes", Journal of Medicinal Chemistry, vol. 47, No. 18, Aug. 1, 2004, pp. 4600-4612, XP055569445.

International Search Report with written opinion, dated Mar. 28, 2019, 11 pages.

Kim et al., "Characterization of Poly(styrene-b-vinylbenzylphosphonic acid) Copolymer by Titration and Thermal Analysis", Macromolecular Research, vol. 15 No. 6, pp. 587-594, 2007.

Monge et al., "Polymerization of Phosphorus-Containing (Meth)acrylate Monomers", published May 7, 2014 http://pubs.rsc.org | doi: 10.1039/9781782624523-00001, 18 pgs.

Schroeder et al., "The Reaction of Phosphorus Trichloride and Oxygen with Polymers", Journal of Polymer Science, vol. 47, Issue 149, pp. 417-433, 1960.

Valentijn A R P M et al: "A novel approach towards the synthesis ofpyrophosphate analogues of farnesyl pyrophoshate", Recueil des Travaux Chimiques des Pays-Bas vol. 113, No. 12, Dec. 12, 1994 (Dec. 12, 1994), pp. 563-566, XP002789048, DOI: 10.1002/RECL.19941131206 [retrieved on Sep. 2, 2010]figure 1; compounds 2, 14.

Amanda J. DeGraw et al., A Photoactive Isoprenoid Diphosphate Analogue Containing a Stable Phosphonate Linkage: Synthesis and Biochemical Studies with Prenyltransferases, Journal of Organic Chemistry, vol. 72, No. 13, pp. 4587-4595, Jun. 22, 2007.

Synthesis and Performance of Phosphono Carboxylic Acid, Yichang Liu, Thesis for the Master Degree in Engineering, Apr. 15, 2016.

* cited by examiner

ORAL CARE COMPOSITIONS COMPRISING PHOSPHONATE AND ANIONIC GROUP CONTAINING POLYMERS

TECHNICAL FIELD OF THE INVENTION

The present invention relates oral care compositions comprising phosphonate and anionic group containing polymers.

BACKGROUND OF THE INVENTION

Chemical structures that interact with multivalent cations in solution and with surfaces containing multivalent cations are useful for manipulation of these systems. Polyphosphates and pyrophosphate, for example, have been used in the oral care industry to help control tartar and reduce the thickness of the pellicle layer on teeth resulting in a slick tooth feel by targeting the amorphous calcium surfaces as well as calcium hydroxy apatite. Similarly, bisphosphonates, and hydroxy-bisphosphonates are active components in osteoporosis pharmaceuticals due to their strong interaction with calcium hydroxy apatite surfaces and are also used as crystal growth inhibitors in dishwashing liquids and boiler systems. Each of these examples suffer from an inherent limitation. Polyphosphates are prone to degradation over time in aqueous solutions at all pH's, ultimately leading to an increase in ortho phosphate in solution. Polyphosphates are, however, generally safe for consumption and find use in different food products. Bisphosphonates and hydroxy-bisphosphonates are, conversely, stable in water for long periods of time, and can, depending upon the nature of the organic group attached to the bisphosphonate carbon, be made quite soluble in organic systems. Bisphosphonates, however, are active to bone surfaces and hence cannot be used in foods or other systems where they might be accidently consumed due to their potent pharmacology. Polymers containing bisphosphonates of sufficient molecular weight to not pass through the intestinal wall would likely not be bone active, however any low molecular weight residual monomers or oligomers that could pass through the intestinal wall make the use of such polymers prohibitive in potential consumable contexts. In addition, since bisphosphonates do not break down readily, their activity can persist in the environment after use.

Therefore, a need still exists for a material that can effectively target multivalent cation containing surfaces, for example calcium hydroxy apatite in oral care applications, that is also water stable and safe for human consumption and can provide a benefit to the surface, for example stain prevention.

SUMMARY OF THE INVENTION

It has surprisingly been found that for use in oral care applications the phosphonate chemical group in a polymer ameliorates the concerns of polyphosphates (not water stable) and bisphosphonates (osteoporosis active), in particular when the polymer also contains an anionic group besides phosphonate like sulfonate. The phosphonate group also has weak interaction with calcium surfaces such as calcium hydroxy apatite, however it is not as strong as a bisphosphonate. This is advantageous as bisphosphonates are bone active and not able to be used in oral care applications where the solution might be ingested. This combination in a polymer along with an anionic group enables formulation into oral care systems to provide a benefit such as stain prevention where non-detrimental effects of consumption and water stability are a must.

In certain embodiments, the present invention is directed to oral care compositions including a polymer comprising a phosphonate group and an anionic group wherein said phosphonate group has the structure of Formula 1:

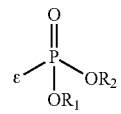

Formula 1 wherein:
  ε is the site of attachment to a carbon atom in the polymer backbone, side group, or side chain;
  $R^1$ is selected from the group consisting of —H, metal salt having Na, K, Ca, Mg, Mn, Zn, Fe, or Sn cation, and amine cation salt,
  $R_2$ is selected from the group consisting of —H, metal salt having Na, K, Ca, Mg, Mn, Zn, Fe, or Sn cation, and amine cation salt,
  and said anionic group is covalently bound to the polymer backbone, side group, or side chain and is sulfonate.

In certain embodiments, at least one monomer used to create the polymer comprises the phosphonate group. In another embodiment, at least one monomer used to create the polymer comprises the anionic group. In another embodiment, at least one monomer used to create said polymer comprises said anionic group and at least one monomer used to create said polymer comprises said phosphonate group. In another embodiment, the phosphonate group is added during a post-polymerization modification.

In certain embodiments, when at least one monomer used to create the polymer comprises the phosphonate group, said at least one monomer has the structure of Formula 2:

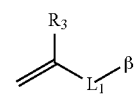

Formula 2 wherein:
  β is the site of attachment to the phosphonate group of Formula 1;
  $R_3$ is selected from the group consisting of —H and —$CH_3$;
  $L_1$ is selected from the group consisting of a chemical bond, arenediyl, and a structure of Formula 3:

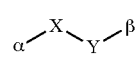

Formula 3 wherein:
  α is the site of attachment to the alkenyl radical in Formula 2;
  β is the site of attachment to the phosphonate group of Formula 1;
  X is selected from the group consisting of the structures in Formulas 4-10;

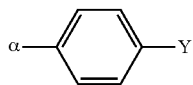

Formula 4

Formula 5

Formula 6

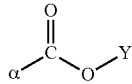

Formula 7

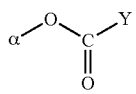

Formula 8

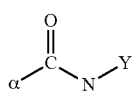

Formula 9

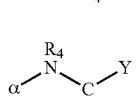

Formula 10 wherein:

$R_4$ is selected from the group consisting of —H, alkyl$_{(C1-8)}$, and phosphonoalkyl; and Y is selected from the group consisting of alkanediyl, alkoxydiyl, alkylaminodiyl and alkenediyl.

In certain embodiments, when at least one monomer used to create the polymer comprises the phosphonate group, and said at least one monomer has the structure of Formula 2, $L_1$ is a covalent bond.

In certain embodiments, $R_1$ is selected from the group consisting of —H, metal salt having Na or K cation, and $R_2$ is selected from the group consisting of —H, metal salt having Na or K cation.

In certain embodiments, when at least one monomer used to create the polymer comprises an anionic group, said at least one monomer further comprises an alkenyl group of the structure of Formula 11:

Formula 11 wherein:

$R_5$ is selected from the group consisting of H or $CH_3$ and $L_2$ is a linking group to the anionic group.

In certain embodiments, when at least one monomer used to create the polymer comprises an anionic group, said at least one monomer further comprises an alkenyl group of the structure of Formula 12:

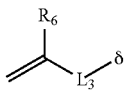

Formula 12 wherein:

$R_6$ is selected from the group consisting of H and alkyl;

δ is the site of attachment to the anionic group;

$L_3$ is selected from the group consisting of a chemical bond, arenediyl, and a structure of Formula 13;

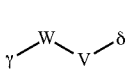

Formula 13 wherein:

γ is the site of attachment to the alkenyl radical;

δ is the site of attachment to the anionic group;

W is selected from the structures in Formulas 14-20:

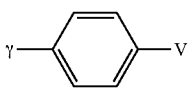

Formula 14

Formula 15

Formula 16

Formula 17

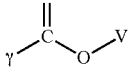

Formula 18

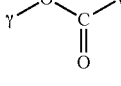

Formula 19

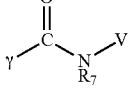

Formula 20 wherein:

$R_7$ is selected from the group consisting of —H, and alkyl$_{(C1-8)}$; and

V is selected from the group consisting of alkanediyl, alkoxydiyl, alkylaminodiyl or alkenediyl.

In certain embodiments, when at least one monomer used to create the polymer comprises the anionic group, and said at least one monomer further comprises an alkenyl group of the structure of Formula 12, $L_3$ is a covalent bond. In certain embodiments, when at least one monomer used to create the polymer comprises the anionic group, and said at least one monomer further comprises an alkenyl group of the structure of Formula 12, W is selected from the group consisting of Formula 14, Formula 17 and Formula 19.

In certain embodiments, when at least one monomer used to create the polymer comprises a phosphonate group, said at least one monomer is selected from the group consisting of vinyl phosphonate and methyl vinyl phosphonate.

In certain embodiments, when at least one monomer used to create the polymer comprises an anionic group, said at least one monomer is selected from the group consisting of vinyl sulfonate, methyl vinyl sulfonate, styrene sulfonate, vinyl benzene sulfonate, 2-acrylamido-2-methyl propane sulfonate (AMPS), and 2-Sulfopropyl Acrylate (SPA).

In certain embodiments, when at least one monomer used to create the polymer comprises a phosphonate group, said at least one monomer is vinyl phosphonate. In certain embodiments, when at least one monomer used to create the polymer comprises an anionic group, said at least one monomer is vinyl sulfonate. In certain embodiments, when at least one monomer used to create said polymer comprises said anionic group and at least one monomer used to create said polymer comprises said phosphonate group, said at least one monomer used to create said polymer comprises said anionic group is vinyl sulfonate and said at least one monomer used to create said polymer comprises said phosphonate group is vinyl phosphonate.

In certain embodiments, when at least one monomer used to create said polymer comprises said anionic group and at least one monomer used to create said polymer comprises said phosphonate group said at least one monomer used to create said polymer comprises said anionic group is vinyl sulfonate and said at least one monomer used to create said polymer comprises said phosphonate group is vinyl phosphonate, the ratio of vinyl sulfonate to vinyl phosphonate ranges from 99.9:0.1 to 0.1:99.9, respectively.

In certain embodiments, when at least one monomer used to create said polymer comprises said anionic group and at least one monomer used to create said polymer comprises said phosphonate group said at least one monomer used to create said polymer comprises said anionic group is vinyl sulfonate and said at least one monomer used to create said polymer comprises said phosphonate group is vinyl phosphonate, the ratio of vinyl sulfonate to vinyl phosphonate ranges from 99:1 to 1:99, respectively.

In certain embodiments, when at least one monomer used to create said polymer comprises said anionic group and at least one monomer used to create said polymer comprises said phosphonate group said at least one monomer used to create said polymer comprises said anionic group is vinyl sulfonate and said at least one monomer used to create said polymer comprises said phosphonate group is vinyl phosphonate, the ratio of vinyl sulfonate to vinyl phosphonate ranges from 90:10 to 10:90, respectively.

In certain embodiments, when at least one monomer used to create said polymer comprises said anionic group and at least one monomer used to create said polymer comprises said phosphonate group said at least one monomer used to create said polymer comprises said anionic group is vinyl sulfonate and said at least one monomer used to create said polymer comprises said phosphonate group is vinyl phosphonate, the ratio of vinyl sulfonate to vinyl phosphonate ranges from 70:30 to 30:70, respectively.

The foregoing summary is not intended to define every aspect of the invention, and additional aspects are described in other sections, such as the Detailed Description. In addition, the invention includes, as an additional aspect, all embodiments of the invention narrower in scope in any way than the variations defined by specific paragraphs set forth herein. For example, certain aspects of the invention that are described as a genus, and it should be understood that every member of a genus is, individually, an aspect of the invention. Also, aspects described as a genus or selecting a member of a genus should be understood to embrace combinations of two or more members of the genus.

These and other features, aspects, and advantages of the present invention will become evident to those skilled in the art from reading of the present disclosure.

DETAILED DESCRIPTION OF THE INVENTION

Figure 1:
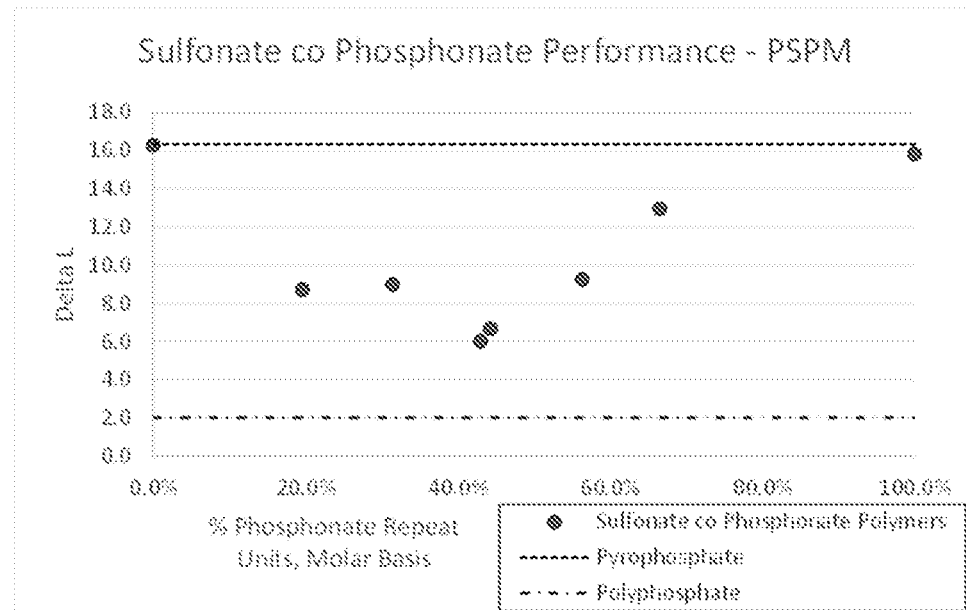
FIG. 1 is a chart showing polymer performance.

While the specification concludes with claims particularly pointing and distinctly claiming the invention, it is believed the present invention will be better understood from the following description.

All percentages herein are by moles of the compositions unless otherwise indicated.

All ratios are molar ratios unless otherwise indicated.

All percentages, ratios, and levels of ingredients referred to herein are based on the actual amount of the ingredient by moles, and do not include solvents, fillers, or other materials with which the ingredient may be combined as commercially available products, unless otherwise indicated.

As used herein, "comprising" means that other steps and other ingredients which do not affect the end result can be added. This term encompasses the terms "consisting of" and "consisting essentially of".

All cited references are incorporated herein by reference in their entireties. Citation of any reference is not an admission regarding any determination as to its availability as prior art to the claimed invention.

Definitions

The terms "site" or "site of attachment" or "point of attachment" all mean an atom having an open valence within a chemical group or defined structural entity that is designated with a symbol such as a simple dash (–) or a lower case letter from the greek alphabet followed by a dash or a line (e.g. α-, β-, etc.) to indicate that the so-designated atom connects to another atom in a separate chemical group via a chemical bond. The symbol "⌇" drawn perpendicular across a bond

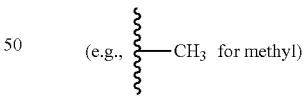

(e.g., ⌇—CH₃ for methyl)

also indicates a point of attachment of a chemical group. It is noted that the point of attachment is typically only identified in this manner for larger chemical groups in order to unambiguously assist the reader in identifying the point of attachment to the atom from which the bond extends. A site or point of attachment on a first chemical group or defined structural entity connects to a site or point of attachment on a second chemical group or defined structural entity via either single, double, or triple covalent bonds in order to satisfy the normal valency of the atoms connected.

The term "radical" when used with a chemical group indicates any connected group of atoms, such as a methyl group, a carboxyl group, or a phosphonate group that is part of a larger molecule.

When used in the context of a chemical group: "hydrogen" means —H; "hydroxy" means —OH; "oxo" means =O; "carbonyl" means —C(=O)—; "carboxy" and "carboxylate" mean —C(=O)OH (also written as —COOH or —CO2H) or a deprotonated form thereof; "amino" means —NH2; "hydroxyamino" means —NHOH; "nitro" means —NO2; "imino" means =NH; "amine oxide" means $N^+O^-$ where N has three covalent bonds to atoms other than O; "hydroxamic" or "hydroxamate" means —C(O)NHOH or a deprotonated form thereof; in a monovalent context "phosphate" means —OP(O)(OH)$_2$ or a deprotonated form thereof: in a divalent context "phosphate" means —OP(O)(OH)O— or a deprotonated form thereof, "phosphonate" means C—P(O)(OH)$_2$ or a deprotonated form thereof, where the C has a normal valence of four and three covalent bonds to atoms other than P; "phosphonate" means a phosphonate that is chemically bound through a shared oxygen atom to at least one phosphate such as but not limited to phosphono-monophosphate C—P(O)(OH)OP(O)(OH)$_2$, phosphono-di-phosphate C—P(O)(OP(O)(OH)$_2$)OP(O)(OH)$_2$, phosphono-cyclodiphosphate

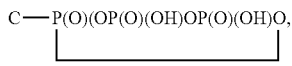

phosphono-pyrophosphate C—P(O)(OH)OP(O)(OH)OP(O)(OH)$_2$, and phosphono-polyphosphate C—P(O)(OH)(OP(O)(OH))$_n$OP(O)(OH)$_2$, where n is an integer between 1 and 100, or a deprotonated form thereof, where the C has a normal valence of four and three covalent bonds to atoms other than P; "phosphinate" means C—P(O)(OH)(C) or a deprotonated form thereof, where both C have a normal valence of four and three additional bonds to atoms other than P; "sulfate" means —OS(O)$_2$OH or deprotonated form thereof, "sulfonate" means CS(O)$_2$OH or a deprotonated form thereof where the C has a normal valence of four and three additional bonds to atoms other than S; "sulfinate" means CS(O)OH or a deprotonated form thereof, where the C has a normal valence of four and three additional bonds to atoms other than S; "mercapto" means —SH; "thio" means =S; "sulfonyl" means —S(O)2-; and "sulfinyl" means —S(O)—.

For the chemical groups and classes below, the following parenthetical subscripts further define the chemical group/class as follows: "(Cn)" defines the exact number (n) of carbon atoms in the chemical group/class. "(C≤n)" defines the maximum number (n) of carbon atoms that can be in the chemical group/class, with the minimum number as small as possible for the chemical group in question, e.g., it is understood that the minimum number of carbon atoms in the chemical group "alkenyl$_{(C≤8)}$" or the chemical class "alkene$_{(C≤8)}$" is two. For example, "alkoxy$_{(C≤8)}$" designates those alkoxy groups having from 1 to 8 carbon atoms. (Cn-n') defines both the minimum (n) and maximum number (n') of carbon atoms in the chemical group. Similarly, alkyl$_{(C≤8)}$ designates those alkyl groups having from 2 to 8 carbon atoms, inclusive.

The term "cation" refers to an atom, molecule, or a chemical group with a net positive charge including single and multiply charged species. Cations can be individual atoms such as metals, non-limiting examples include $Na^+$ or $Ca^{+2}$, individual molecules, non-limiting examples include $(CH_3)_4N^+$, or a chemical group, non limiting examples include $-N(CH_3)_3^+$. The term "amine cation" refers to a particular molecular cation, of the form $NR_4^+$ where the four substituting R moieties can be independently selected from H and alkyl, non-limiting examples include $NH_4^+$ (ammonium), $CH_3NH_3^+$ (methylammonium), $CH_3CH_2NH_3^+$ (ethylammonium), $(CH_3)_2NH_2^+$ (dimethylammonium), $(CH_3)_3NH^+$ (trimethyl ammonium), and $(CH_3)_4N^+$ (tetramethylammonium).

The term "anion" refers to an atom, molecule, or chemical group with a net negative charge including single and multiply charged species. Anions can be individual atoms, for example but not limited to halides $F^-$, $Cl^-$, $Br^-$, individual molecules, non limiting examples include $CO_3^{-2}$, $H_2PO_4^-$, $HPO_4^{-2}$, $PO_4^{-3}$, $HSO_4^+$, $SO_4^{-2}$, or a chemical group, non limiting examples include sulfate, phosphate, sulfonate, phosphonate, phosphinate, sulfonate, mercapto, carboxylate, amine oxide, hydroxamate and hydroxyl amino. Deprotonated forms of previously defined chemical groups are considered anionic groups if the removal of the proton results in a net negative charge. In solutions, chemical groups are capable of losing a proton and become anionic as a function of pH according to the Henderson-Hasselbach equation ($pH=pKa+\log_{10}([A^-]/[HA]$; where [HA] is the molar concentration of an undissociated acid and [A-] is the molar concentration of this acid's conjugate base). When the pH of the solution equals the pKa value of functional group, 50% of the functional group will be anionic, while the remaining 50% will have a proton. Typically, a functional group in solution can be considered anionic if the pH is at or above the pKa of the functional group.

The term "salt" or "salts" refers to the charge neutral combination of one or more anions and cations. For example, when R is denoted as a salt for the carboxylate group, —COOR, it is understood that the carboxylate (—COO—) is an anion with a negative charge −1, and that the R is a cation with a positive charge of +1 to form a charge neutral entity with one anion of charge −1, or R is a cation with a positive charge of +2 to form a charge neutral entitity with two anions both of −1 charge.

The term "saturated" as used herein means the chemical compound or group so modified has no carbon-carbon double and no carbon-carbon triple bonds, except as noted below. In the case of substituted versions of saturated chemical groups, one or more carbon oxygen double bond or a carbon nitrogen double bond may be present. When such a bond is present, then carbon-carbon double bonds that may occur as part of keto-enol tautomerism or imine/enamine tautomerism are not precluded.

The term "aliphatic" when used without the "substituted" modifier signifies that the chemical compound/group so modified is an acyclic or cyclic, but non-aromatic hydrocarbon chemical compound or group. In aliphatic chemical compounds/groups, the carbon atoms can be joined together in straight chains, branched chains, or non-aromatic rings (alicyclic). Aliphatic chemical compounds/groups can be saturated, that is joined by single bonds (alkanes/alkyl), or unsaturated, with one or more double bonds (alkenes/alkenyl), or with one or more triple bonds (alkynes/alkynyl).

The term "alkyl" when used without the "substituted" modifier refers to a monovalent saturated aliphatic group with a carbon atom as the point of attachment, a linear or branched, cyclo, cyclic, or acyclic structure, and no atoms other than carbon and hydrogen. Thus, as used herein cycloalkyl is a subset of alkyl, with the carbon atom that forms the point of attachment also being a member of one or more non-aromatic ring structures wherein the cycloalkyl group consists of no atoms other than carbon and hydrogen. As used herein, the term does not preclude the presence of one or more alkyl groups (carbon number limitation permitting) attached to the ring or ring system. The groups —CH₃ (Me), —CH₂CH₃ (Et), —CH₂CH₂CH₃ (n-Pr or propyl), —CH(CH₃)₂ (i-Pr, ᶦPr, or isopropyl), —CH(CH₂)₂ (cyclopropyl), —CH₂CH₂CH₂CH₃ (n-Bu), —CH(CH₃)CH₂CH₃ (sec-butyl), —CH₂CH(CH₃)₂ (isobutyl), —C(CH₃)₃ (tert-butyl, t-butyl, t-Bu, or tBu), —CH₂C(CH₃)₃ (neo-pentyl), cyclobutyl, cyclopentyl, cyclohexyl, and cyclohexylmethyl are non-limiting examples of alkyl groups. The term "alkanediyl" when used without the "substituted" modifier refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH₂— (methylene), —CH₂CH₂—, —CH₂C(CH₃)₂CH₂—, and —CH₂CH₂CH₂— are non-limiting examples of alkanediyl groups. The term "alkylidene" when used without the "substituted" modifier refers to the divalent group =CRR' in which R and R' are independently hydrogen, alkyl, or R and R' are taken together to represent an alkanediyl having at least two carbon atoms. Non-limiting examples of alkylidene groups include: =CH₂, =CH(CH₂CH₃), and =C(CH₃)₂. An "alkane" refers to the compound H—R, wherein R is alkyl as this term is defined above. When any of these terms is used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O) CH₃, —NHCH₃, —NHCH₂CH₃, —N(CH₃)₂, —C(O)NH₂, —OC(O)CH₃, —S(O)₂NH₂, —P(O)(OH)₂, —P(O)(OH)OP (O)(OH)₂, —OP(O)(OH)₂, —OP(O)(OH)OP(O)(OH)₂, —S(O)₂(OH), or —OS(O)₂(OH). The following groups are non-limiting examples of substituted alkyl groups: —CH₂OH, —CH₂Cl, —CF₃, —CH₂CN, —CH₂C(O)OH, —CH₂C(O)OCH₃, —CH₂C(O)NH₂, —CH₂C(O)CH₃, —CH₂OCH₃, —CH₂OC(O)CH₃, —CH₂NH₂, —CH₂N (CH₃)₂, —CH₂CH₂Cl, —CH₂P(O)(OH)₂, —CH₂P(O)(OH) OP(O)(OH)₂, —CH₂S(O)₂(OH), and —CH₂OS(O)₂(OH). The term "haloalkyl" is a subset of substituted alkyl, in which one or more hydrogen atoms has been substituted with a halo group and no other atoms aside from carbon, hydrogen and halogen are present. The group, —CH₂Cl is a non-limiting example of a haloalkyl. The term "fluoroalkyl" is a subset of substituted alkyl, in which one or more hydrogen has been substituted with a fluoro group and no other atoms aside from carbon, hydrogen and fluorine are present. The groups, —CH₂F, —CF₃, and —CH₂CF₃ are non-limiting examples of fluoroalkyl groups.

The term "phosphonoalkyl" is a subset of substituted alkyl, in which one or more of the hydrogen has been substituted with a phosphonate group and no other atoms aside from carbon, hydrogen, phosphorous, and oxygen are present. The groups, —CH₂P(O)(OH)₂, and —CH₂CH₂P (O)(OH)₂, and the corresponding deprotonated forms thereof, are non-limiting examples of a phosphonoalkyl.

The term "phosphono(phosphate)alkyl" is a subset of substituted alkyl, in which one or more of the hydrogen has been substituted with a phosphonate group and no other atoms aside from carbon, hydrogen, phosphorous, and oxygen are present. The groups, —CH₂P(O)(OH)OP(O)(OH)₂, and —CH₂CH₂P(O)(OH)OP(O)(OH)₂, and corresponding deprotonated forms thereof, are non-limiting examples of phosphono(phosphate)alkyl.

The term "sulfonoalkyl" is a subset of substituted alkyl, in which one or more of the hydrogen has been substituted with a sulfonate group and no other atoms aside from carbon, hydrogen, sulfur, and oxygen are present. The groups, —CH₂S(O)₂OH and —CH₂CH₂S(O)₂OH, and the corresponding deprotonated forms thereof, are non-limiting examples of a sulfonoalkyl.

The term "alkenyl" when used without the "substituted" modifier refers to an monovalent unsaturated aliphatic group with a carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH=CH₂ (vinyl), —C(CH₃)=CH₂ (methyl-vinyl), —CH=CHCH₃, —CH=CHCH₂CH₃, —CH₂CH=CH₂ (allyl), —CH₂CH=CHCH₃, and —CH=CHCH=CH₂. The term "alkenediyl" when used without the "substituted" modifier refers to a divalent unsaturated aliphatic group, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, >C=CH₂ (vinylidine), —CH=CH—, —CH=C(CH₃)CH₂—, and —CH=CHCH₂—, are non-limiting examples of alkenediyl groups. It is noted that while the alkenediyl group is aliphatic, once connected at both ends, this group is not precluded from forming part of an aromatic structure. The terms "alkene" or "olefin" are synonymous and refer to a compound having the formula H—R, wherein R is alkenyl as this term is defined above. A "terminal alkene" refers to an alkene having just one carbon-carbon double bond, wherein that bond forms a vinyl group at one end of the molecule. When any of these terms are used with the "substituted" modifier one or more hydrogen atom has been independently replaced by —OH, —F, —Cl, —Br, —I, —NH, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃, or —S(O)₂NH₂. The groups, —CH=CHF, —CH=CHCl and —CH=CHBr, are non-limiting examples of substituted alkenyl groups.

The term "alkynyl" when used without the "substituted" modifier refers to an monovalent unsaturated aliphatic group with a carbon atom as the point of attachment, a linear or branched, cyclo, cyclic or acyclic structure, at least one carbon-carbon triple bond, and no atoms other than carbon and hydrogen. As used herein, the term alkynyl does not preclude the presence of one or more non-aromatic carbon-carbon double bonds. The groups, —C≡CH, —C≡CCH₃, and —CH₂C≡CCH₃, are non-limiting examples of alkynyl groups. An "alkyne" refers to the compound H—R, wherein R is alkynyl. When any of these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃, or —S(O)₂NH₂.

The term "aryl" when used without the "substituted" modifier refers to a monovalent unsaturated aromatic group with an aromatic carbon atom as the point of attachment, said carbon atom forming part of a one or more six membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. Non-limiting examples of aryl groups include phenyl (-Ph), methylphenyl, (dimethyl)phenyl, —C₆H₄CH₂CH₃ (ethylphenyl), naphthyl, and a monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl, aryl or aralkyl groups (carbon number limitation permitting) attached to the first aromatic ring or any additional aromatic ring present. If more than one ring is present, the rings may be fused or unfused. Unfused rings may be connected via one or more of the following: a covalent bond, alkanediyl, or alkenediyl groups (carbon number limitation permitting). Non-limiting examples of arenediyl groups include:

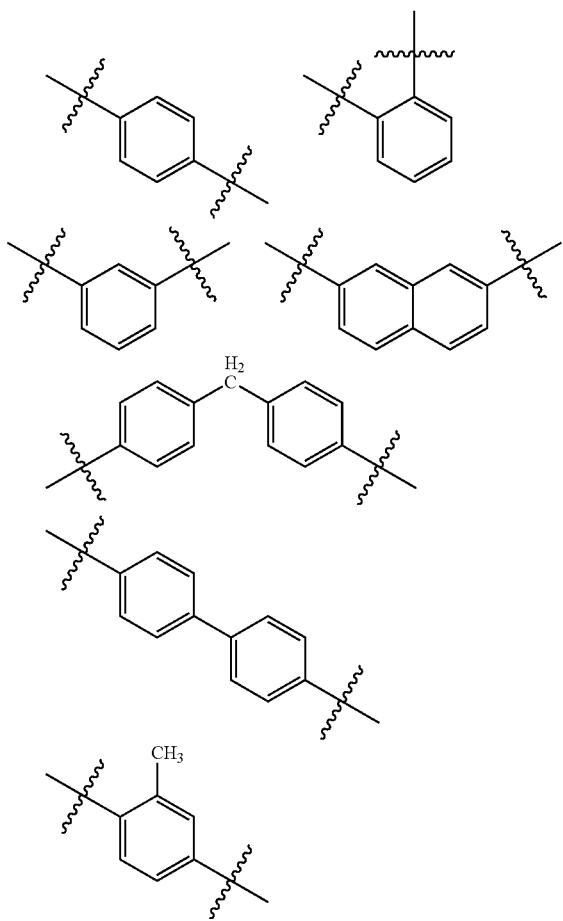

An "arene" refers to the compound H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃, or —S(O)₂NH₂.

The term "acyl" when used without the "substituted" modifier refers to the group —C(O)R, in which R is a hydrogen, alkyl, aryl, aralkyl or heteroaryl, as those terms are defined above. The groups, —CHO (formyl), —C(O)CH₃ (acetyl, Ac), —C(O)CH₂CH₃, —C(O)CH₂CH₂CH₃, —C(O)CH(CH₃)₂, —C(O)CH(CH₂)₂, —C(O)C₆H₅, —C(O)C₆H₄CH₃, —C(O)CH₂C₆H₅, —C(O)(imidazolyl) are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkane, as defined above, wherein at least one of the hydrogen atoms has been replaced with a —CHO group. When any of these terms are used with the "substituted" modifier one or more hydrogen atom (including a hydrogen atom directly attached the carbonyl or thiocarbonyl group, if any) has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃, or —S(O)₂NH₂. The groups, —C(O)CH₂CF₃, —CO₂H (carboxyl), —CO₂CH₃(methylcarboxyl), —CO₂CH₂CH₃, —C(O)NH₂ (carbamoyl), and —CON(CH₃)₂, are non-limiting examples of substituted acyl groups.

The term "alkoxy" when used without the "substituted" modifier refers to the group —OR, in which R is an alkyl, as that term is defined above. Non-limiting examples of alkoxy groups include: —OCH₃ (methoxy), —OCH₂CH₃ (ethoxy), —OCH₂CH₂CH₃, —OCH(CH₃)₂ (isopropoxy), —O(CH₃)₃ (tert-butoxy), —OCH(CH₂)₂, —O-cyclopentyl, and —O-cyclohexyl. The terms "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is alkenyl, alkynyl, aryl, aralkyl, heteroaryl, heterocycloalkyl, and acyl, respectively. The term "alkoxydiyl" refers to the divalent group —O-alkanediyl-, —O-alkanediyl-O—, or -alkanediyl-O-alkanediyl-. The term "alkanediyl-alkoxy" refers to -alkanediyl-O-alkyl. A non-limiting example of alkanedyl-alkoxy is CH₂—CH₂—O—CH₂—CH₃. The term "alkylthio" and "acylthio" when used without the "substituted" modifier refers to the group —SR, in which R is an alkyl and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group. When any of these terms is used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃, or —S(O)₂NH₂.

The term "alkylamino" when used without the "substituted" modifier refers to the group —NHR, in which R is an alkyl, as that term is defined above. Non-limiting examples of alkylamino groups include: —NHCH₃ and —NHCH₂CH₃. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH₃)₂, —N(CH₃)(CH₂CH₃), and N-pyrrolidinyl. The terms "alkoxyamino", "alkenylamino", "alkynylamino", "arylamino", "aralkylamino", "heteroarylamino", "heterocycloalkylamino" and "alkylsulfonylamino" when used without the "substituted" modifier, refers to groups, defined as —NHR, in which R is alkoxy, alkenyl, alkynyl, aryl, aralkyl, heteroaryl, heterocycloalkyl, and alkylsulfonyl, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. The term "alkylimino" when used without the "substituted" modifier refers to the divalent group =NR, in which R is an alkyl, as that term is defined above. The term "alkylaminodiyl" refers to the divalent group —NH-alkanediyl-, —NH-alkanediyl-NH—, or -alkanediyl-NH-alkanediyl-. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups —NHC(O)OCH$_3$ and —NHC(O)NHCH$_3$ are non-limiting examples of substituted amido groups.

The terms "alkylsulfonyl" and "alkylsulfinyl" when used without the "substituted" modifier refers to the groups —S(O)$_2$R and —S(O)R, respectively, in which R is an alkyl, as that term is defined above. The terms "alkenylsulfonyl", "alkynylsulfonyl", "aralkylsulfonyl", "arylsulfonyl", "heteroarylsulfonyl", and "heterocycloalkylsulfonyl" are defined in an analogous manner. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "alkylphosphate" when used without the "substituted" modifier refers to the group —OP(O)(OH)(OR) or a deprotonated form thereof, in which R is an alkyl, as that term is defined above. Nonlimiting examples of alkylphosphate groups include: —OP(O)(OH)(OMe) and —OP(O)(OH)(OEt). The term "dialkylphosphate" when used without the "substituted" modifier refers to the group —OP(O)(OR)(OR'), in which R and R' can be the same or different alkyl groups, or R and R' can be taken together to represent an alkanediyl. Non-limiting examples of dialkylphosphate groups include: —OP(O)(OMe)$_2$, —OP(O)(OEt)(OMe) and —OP(O)(OEt)$_2$. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

Linking group means either a covalent bond between two other defined groups, or a series of covalently bound atoms that connect two other defined groups where in the series of covalently bound atoms have no open valences other than the sites of attachment to the two other defined groups. Non-limiting examples of a linking group include a covalent bond, alkanediyl, alkenediyl, arenediyl, alkoxydiyl, and alkylaminodiyl.

As used herein, a "chiral auxiliary" refers to a removable chiral group that is capable of influencing the stereoselectivity of a reaction. Persons of skill in the art are familiar with such compounds, and many are commercially available.

Other abbreviations used herein are as follows: DMSO, dimethyl sulfoxide; DMF, dimethylformamide; MeCN, acetonitrile; MeOH, methanol; EtOH, ethanol; EtOAc, ethyl acetate; tBuOH, tert-butanol; iPrOH, isopropanol; cHexOH, cyclohexanol; Ac$_2$O, acetic anhydride; AcOOH, peracetic acid; HCO$_2$Et, ethyl formate; THF, tetrahydrofuran; MTBE, methyl tert-butyl ether; DME, dimethoxyethane; NBS, N-bromosuccinimide; CDI, carbonyldiimidazole; DIEA, diisopropylethylamine; TEA, triethylamine; DMAP, dimethylaminopyridine; NaOH, sodium hydroxide; AAPH, 2,2'-azobis(2-methylpropanamidine) dihydrochloride; CTA, 1-Octanethiol; APS, ammonium persulfate; TMP, trimethyl phosphate; VPA, vinyl phosphonic acid; VPP, vinyl phosphono-monophosphate; VPPP, vinyl phosphono-pyro-phosphate MVPP, methyl-vinyl phosphono-monophosphate; SVS, sodium vinyl sulfonate; AMPS, sodium 2-acrylamido-2-methyl propane sulfonic acid; SPA, 3-sulfopropyl acrylate potassium salt; 22A2MPA2HCl, 2,2'-azobis (2-methylpropionamidine) dihydrochloride; VBPP, (4-vinylbenzyl)monophosphono-phosphate; VSME, vinyl sulfonate methyl ester; NaOMe, sodium methoxide; NaCl, sodium chloride; DMVP, dimethyl vinyl phosphonate A "monomer molecule" is defined by the International Union of Pure and Applied Chemistry (IUPAC) as "A molecule which can undergo polymerization thereby contributing constitutional units to the essential structure of a macromolecule." A polymer is a macromolecule.

A "polymer backbone" or "main chain" is defined by IUPAC as "That linear chain to which all other chains, long or short, or both may be regarded as being pendant" with the note that "Where two or more chains could equally be considered to be the main chain, that one is selected which leads the simplest representation of the molecule." Backbones can be of different chemical compositions depending upon the starting materials from which they are made. Common backbones from chemically and biologically synthesized polymers include alkanes, typically from vinyl or methyl vinyl polymerizations or cationic and anionic polymerizations, poly esters, from condensation polymerizations, poly amides, such as poly peptides from polymerizations involving amidation reactions, and poly ethoxylates from epoxide ring opening.

A "pendant group" or "side group" is defined by IUPAC as "An offshoot, neither oligomeric nor polymeric from a chain." A side group as such does not include a linear repeated unit.

A "polymer side chain" or "pendant chain" is defined by IUPAC as "An oligomeric or polymeric offshoot from a macromolecular chain" with the additional notes that "An oligomeric branch may be termed a short chain branch" and "A polymeric branch may be termed a long chain branch".

"Post-polymerization modification" is defined as any reaction or treatment of a polymer that takes place following polymerization. Post-polymerization modifications include reactions to chemical groups within or attached to the polymer backbone, pendant group, or polymer side chains.

By "personal care composition" is meant a product, which in the ordinary course of usage is applied to or contacted with a body surface to provide a beneficial effect. Body surface includes skin, for example dermal or mucosal; body surface also includes structures associated with the body surface for example hair, teeth, or nails. Examples of personal care compositions include a product applied to a human body for improving appearance, cleansing, and odor control or general aesthetics. Non-limiting examples of personal care compositions include oral care compositions, such as, dentifrice, mouth rinse, mousse, foam, mouth spray, lozenge, chewable tablet, chewing gum, tooth whitening strips, floss and floss coatings, breath freshening dissolvable strips, denture care product, denture adhesive product; after shave gels and creams, pre-shave preparations, shaving gels, creams, or foams, moisturizers and lotions; cough and cold compositions, gels, gel caps, and throat sprays; leave-on skin lotions and creams, shampoos, body washes, body rubs, such as Vicks Vaporub; hair conditioners, hair dyeing and bleaching compositions, mousses, shower gels, bar soaps, antiperspirants, deodorants, depilatories, lipsticks, foundations, mascara, sunless tanners and sunscreen lotions; feminine care compositions, such as lotions and lotion compositions directed towards absorbent articles; baby care compositions directed towards absorbent or disposable articles; and oral cleaning compositions for animals, such as dogs and cats.

The term "dentifrice", as used herein, includes tooth or subgingival-paste, gel, or liquid formulations unless otherwise specified. The dentifrice composition may be a single phase composition or may be a combination of two or more separate dentifrice compositions. The dentifrice composition may be in any desired form, such as deep striped, surface striped, multilayered, having a gel surrounding a paste, or any combination thereof. Each dentifrice composition in a dentifrice comprising two or more separate dentifrice compositions may be contained in a physically separated compartment of a dispenser and dispensed side-by-side.

The term "dispenser", as used herein, means any pump, tube, or container suitable for dispensing compositions such as dentifrices.

The term "teeth", as used herein, refers to natural teeth as well as artificial teeth or dental prosthesis.

The term "orally acceptable carrier or excipients" includes safe and effective materials and conventional additives used in oral care compositions including but not limited to fluoride ion sources, anti-calculus or anti-tartar agents, buffers, abrasives such as silica, alkali metal bicarbonate salts, thickening materials, humectants, water, surfactants, titanium dioxide, flavorants, sweetening agents, xylitol, coloring agents, and mixtures thereof.

Herein, the terms "tartar" and "calculus" are used interchangeably and refer to mineralized dental plaque biofilms.

As used herein, the word "or" when used as a connector of two or more elements is meant to include the elements individually and in combination; for example X or Y, means X or Y or both.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The above definitions supersede any conflicting definition in any reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

Phosphonate and Anionic Containing Polymers

The present invention is directed to a polymer comprising a phosphonate group and an anionic group for use in oral care applications. It is recognized that the phosphonate group can be anionic in nature depending upon the substituents upon it and the environment into which it is placed. For the purpose of clarity, anionic group in this application refers to an anionic group other than phosphonate. Homopolymers of phosphonate polymers, such as polyvinyl phosphonate have been described previously for use in oral care applications, see US20050271602A1. As will be shown here, the combination of an anionic group such as sulfonate in addition to the phosphonate in a polymer is able to prevent staining on hydroxy apatite and on grown plaque. This inhibition is considerably better than that seen from a phosphonate containing polymer on its own.

In certain embodiments, the present invention is directed to oral care compositions including a polymer comprising a phosphonate group and an anionic group wherein said phosphonate group has the structure of Formula 1:

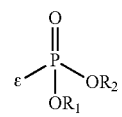

Formula 1 wherein:
ε is the site of attachment to a carbon atom in the polymer backbone, side group, or side chain;
$R_1$ is selected from the group consisting of —H, metal salt having Na, K, Ca, Mg, Mn, Zn, Fe, or Sn cation, and amine cation salt,
$R_2$ is selected from the group consisting of —H, metal salt having Na, K, Ca, Mg, Mn, Zn, Fe, or Sn cation, and amine cation salt,
and said anionic group is covalently bound to the polymer backbone, side group, or side chain and is sulfonate.

In certain embodiments, at least one monomer used to create the polymer comprises the phosphonate group. In another embodiment, at least one monomer used to create the polymer comprises the anionic group. In another embodiment, at least one monomer used to create said polymer comprises said anionic group and at least one monomer used to create said polymer comprises said phosphonate group. In another embodiment, the phosphonate group is added during a post-polymerization modification.

In certain embodiments of the polymer, $R_1$, and $R_2$, are independently selected from the group consisting of H, Na salt, and K salt. In certain embodiments of the polymer, $R_1$, and $R_2$, are independently selected from the group consisting of H, Na salt, K salt, Zn salt, Ca salt, Sn salt, and amine cation salt.

In certain embodiments, when at least one monomer used to create the polymer comprises the phosphonate group, said at least one monomer has the structure of Formula 2:

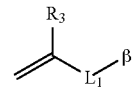

Formula 2 wherein:
β is the site of attachment to the phosphonate group of Formula 1;
$R_3$ is selected from the group consisting of —H and —$CH_3$;
$L_1$ is selected from the group consisting of a chemical bond, arenediyl, and a structure of Formula 3:

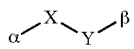

Formula 3 wherein:
α is the site of attachment to the alkenyl radical in Formula 2;
β is the site of attachment to the phosphonate group of Formula 1;
X is selected from the group consisting of the structures in Formulas 4-10;

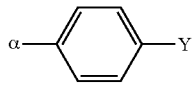

Formula 4

Formula 5

Formula 6

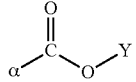

Formula 7

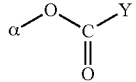

Formula 8

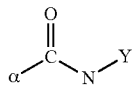

Formula 9

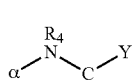

Formula 10 wherein:
$R_4$ is selected from the group consisting of —H, alkyl$_{(C1-8)}$, and phosphonoalkyl; and
Y is selected from the group consisting of alkanediyl, alkoxydiyl, alkylaminodiyl and alkenediyl.

In certain embodiments, when at least one monomer used to create the polymer comprises the phosphonate group and has the structure of Formula 2, $R_3$ of Formula 2 is H. In certain embodiments, when at least one monomer used to create the polymer comprises the phosphonate group and has the structure of Formula 2, $R_3$ of Formula 2 is $CH_3$.

In certain embodiments, when at least one monomer used to create the polymer comprises the phosphonate group, and said at least one monomer has the structure of Formula 2, $L_1$ is a covalent bond.

In another embodiment, when at least one monomer used to create the polymer comprises the phosphonate group, and said at least one monomer has the structure of Formula 2, $L_1$ has the structure of Formula 3. In another embodiment, when at least one monomer used to create the polymer comprises the phosphonate group, said at least one monomer has the structure of Formula 2, and $L_1$ has the structure of Formula 3, the structure of X is selected from the group consisting of Formula 4, Formula 7 and Formula 9. In another embodiment, when at least one monomer used to create the polymer comprises the phosphonate group, said at least one monomer has the structure of Formula 2, and $L_1$ has the structure of Formula 3, X has the structure of of Formula 4. In another embodiment, when at least one monomer used to create the polymer comprises the phosphonate group, said at least one monomer has the structure of Formula 2, and $L_1$ has the structure of Formula 3, X has the structure of Formula 7. In another embodiment, when at least one monomer used to create the polymer comprises the phosphonate group, said at least one monomer has the structure of Formula 2, and $L_1$ has the structure of Formula 3, X has the structure of of Formula 9. In another embodiment, when at least one monomer used to create the polymer comprises the phosphonate group, said at least one monomer has the structure of Formula 2, and $L_1$ has the structure of Formula 3, X has the structure of of Formula 5. In another embodiment, when at least one monomer used to create the polymer comprises the phosphonate group, said at least one monomer has the structure of Formula 2, and $L_1$ has the structure of Formula 3, X has the structure of of Formula 4 and Y is alkanediyl. In another embodiment, when at least one monomer used to create the polymer comprises the phosphonate group, said at least one monomer has the structure of Formula 2, and $L_1$ has the structure of Formula 3, X has the structure of of Formula 7 and Y is selected from the group consisting of alkanediyl and alkoxydiyl. In another embodiment, when at least one monomer used to create the polymer comprises the phosphonate group, said at least one monomer has the structure of Formula 2, and $L_1$ has the structure of Formula 3, X has the structure of of Formula 9 and Y is alkanediyl. In another embodiment, when at least one monomer used to create the polymer comprises the phosphonate group, said at least one monomer has the structure of Formula 2, and $L_1$ has the structure of Formula 3, X has the structure of of Formula 5 and Y is alkanediyl.

In certain embodiments, when at least one monomer used to create the polymer comprises an anionic group, said at least one monomer further comprises an alkenyl group of the structure of Formula 11:

Formula 11 wherein:
$R_5$ is selected from the group consisting of H or $CH_3$ and
$L_2$ is a linking group to the anionic group.

In certain embodiments, when at least one monomer used to create the polymer comprises an anionic group and said at least one monomer further comprises an alkenyl group of the structure of Formula 11, $R_5$ is H. In another embodiment, when at least one monomer used to create the polymer comprises an anionic group and said at least one monomer further comprises an alkenyl group of the structure of Formula 11, $R_5$ is $CH_3$.

In certain embodiments, when at least one monomer used to create the polymer comprises an anionic group, said at least one monomer further comprises an alkenyl group of the structure of Formula 12:

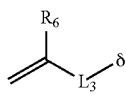

Formula 12 wherein:
 $R_6$ is selected from the group consisting of H and alkyl;
 δ is the site of attachment to the anionic group;
 $L_3$ is selected from the group consisting of a chemical bond, arenediyl, and a structure of Formula 13;

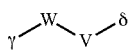

Formula 13 wherein:
 γ is the site of attachment to the alkenyl radical;
 δ is the site of attachment to the anionic group;
 W is selected from the structures in Formulas 14-20:

Formula 14

Formula 15

Formula 16

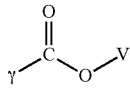

Formula 17

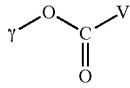

Formula 18

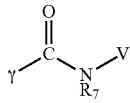

Formula 19

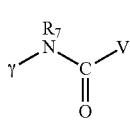

Formula 20 wherein:
 $R_7$ is selected from the group consisting of —H, and alkyl(ci-s); and
 V is selected from the group consisting of alkanediyl, alkoxydiyl, alkylaminodiyl or alkenediyl.

In certain embodiments, when at least one monomer used to create the polymer comprises an anionic group and said at least one monomer further comprises an alkenyl group of the structure of Formula 12, $R_6$ is H. In another embodiment, when at least one monomer used to create the polymer comprises an anionic group and said at least one monomer further comprises an alkenyl group of the structure of Formula 12, $R_6$ is $CH_3$. In another embodiment, when at least one monomer used to create the polymer comprises an anionic group and said at least one monomer further comprises an alkenyl group of the structure of Formula 12, $L_3$ is a covalent bond. In another embodiment, when at least one monomer used to create the polymer comprises an anionic group and said at least one monomer further comprises an alkenyl group of the structure of Formula 12, $R_6$ is H and $L_3$ is a covalent bond. In another embodiment, when at least one monomer used to create the polymer comprises an anionic group and said at least one monomer further comprises an alkenyl group of the structure of Formula 12, $R_6$ is $CH_3$ and $L_3$ is a covalent bond.

In certain embodiments, when at least one monomer used to create the polymer comprises an anionic group and said at least one monomer further comprises an alkenyl group of the structure of Formula 12, $L_3$ has the structure of Formula 13 and W has the structure of Formula 14. In another embodiment, when at least one monomer used to create the polymer comprises an anionic group and said at least one monomer further comprises an alkenyl group of the structure of Formula 12, $L_3$ has the structure of Formula 13 and W has the structure of Formula 17. In another embodiment, when at least one monomer used to create the polymer comprises an anionic group and said at least one monomer further comprises an alkenyl group of the structure of Formula 12, $L_3$ has the structure of Formula 13 and W has the structure of Formula 19. In certain embodiments, when at least one monomer used to create the polymer comprises an anionic group and said at least one monomer further comprises an alkenyl group of the structure of Formula 12, $L_3$ has the structure of Formula 13 and W has the structure of Formula 14 and V is alkanediyl. In another embodiment, when at least one monomer used to create the polymer comprises an anionic group and said at least one monomer further comprises an alkenyl group of the structure of Formula 12, $L_3$ has the structure of Formula 13 and W has the structure of Formula 17 and V is alkanediyl. In another embodiment, when at least one monomer used to create the polymer comprises an anionic group and said at least one monomer further comprises an alkenyl group of the structure of Formula 12, $L_3$ has the structure of Formula 13 and W has the structure of Formula 19 and V is alkanediyl.

In certain embodiments, when at least one monomer used to create the polymer comprises an anionic group and said at least one monomer further comprises an alkenyl group of the structure of Formula 12, $L_3$ has the structure of Formula 13 and W is selected from the group consisting of Formula 14, Formula 17 and Formula 19.

In certain embodiments, when at least one monomer used to create the polymer comprises an phosphonate group, said at least one monomer is selected from the group consisting of vinyl phosphonate and methyl vinyl phosphonate.

In certain embodiments, when at least one monomer used to create the polymer comprises an anionic group, said at least one monomer is selected from the group consisting of vinyl sulfonate, methyl vinyl sulfonate, styrene sulfonate, vinyl benzene sulfonate, 2-acrylamido-2-methyl propane sulfonate (AMPS), and 2-Sulfopropyl Acrylate (SPA).

In certain embodiments, when at least one monomer used to create the polymer comprises an phosphonate group, said at least one monomer is vinyl phosphonate. In certain embodiments, when at least one monomer used to create the polymer comprises an anionic group, said at least one monomer is vinyl sulfonate. In certain embodiments, when at least one monomer used to create said polymer comprises said anionic group and at least one monomer used to create said polymer comprises said phosphonate group, said at least one monomer used to create said polymer comprises said anionic group is vinyl sulfonate and said at least one monomer used to create said polymer comprises said phosphonate group is vinyl phosphonate.

In certain embodiments, when at least one monomer used to create said polymer comprises said anionic group and at least one monomer used to create said polymer comprises said phosphonate group said at least one monomer used to create said polymer comprises said anionic group is vinyl sulfonate and said at least one monomer used to create said polymer comprises said phosphonate group is vinyl phosphonate, the ratio of vinyl sulfonate to vinyl phosphonate ranges from 99.9:0.1 to 0.1:99.9, respectively.

In certain embodiments, when at least one monomer used to create said polymer comprises said anionic group and at least one monomer used to create said polymer comprises said phosphonate group said at least one monomer used to create said polymer comprises said anionic group is vinyl sulfonate and said at least one monomer used to create said polymer comprises said phosphonate group is vinyl phosphonate, the ratio of vinyl sulfonate to vinyl phosphonate ranges from 99:1 to 1:99, respectively.

In certain embodiments, when at least one monomer used to create said polymer comprises said anionic group and at least one monomer used to create said polymer comprises said phosphonate group said at least one monomer used to create said polymer comprises said anionic group is vinyl sulfonate and said at least one monomer used to create said polymer comprises said phosphonate group is vinyl phosphonate, the ratio of vinyl sulfonate to vinyl phosphonate ranges from 90:10 to 10:90, respectively.

In certain embodiments, when at least one monomer used to create said polymer comprises said anionic group and at least one monomer used to create said polymer comprises said phosphonate group said at least one monomer used to create said polymer comprises said anionic group is vinyl sulfonate and said at least one monomer used to create said polymer comprises said phosphonate group is vinyl phosphonate, the ratio of vinyl sulfonate to vinyl phosphonate ranges from 70:30 to 30:70, respectively.

Another embodiment of the present invention is an oral care composition comprising polymer which in this context is meant to include oligomers such as dimers trimers and tetramers. The polymer includes a phosphonate group and anionic group with the structure of Formula 23:

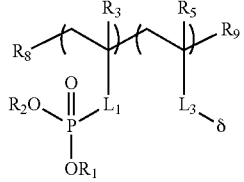

Formula 21 wherein:
R$_1$ is selected from the group consisting of —H, alkyl, alkanediyl-alkoxy, metal salt having Na, K, Ca, Mg, Mn, Zn, Fe, or Sn cation, and amine cation salt;
R$_2$ is selected from the group consisting of —H, alkyl, alkanediyl-alkoxy, metal salt having Na, K, Ca, Mg, Mn, Zn, Fe, or Sn cation, and amine cation salt;

R$_3$ is selected from the group consisting of —H and —CH$_3$;
L$_1$ is selected from the group consisting of a chemical bond, arenediyl, and a structure of Formula 3:

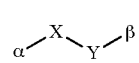

Formula 3 wherein:
α is the site of attachment to the polymer backbone;
β is the site of attachment to the phosphonophosphate;
X is selected from the group consisting of the structures in Formulas 4-10;

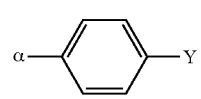

Formula 4

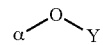

Formula 5

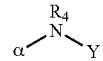

Formula 6

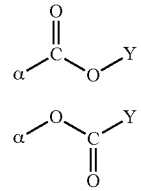

Formula 7

Formula 8

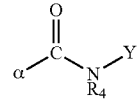

Formula 9

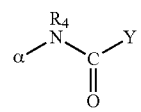

Formula 10 wherein:
R$_4$ is selected from the group consisting of —H, alkyl$_{(C1-8)}$, phosphonoalkyl, and phosphono(phosphate)alkyl; and
Y is selected from the group consisting of alkanediyl, alkoxydiyl, alkylaminodiyl and alkenediyl;
R$_5$ is selected from the group consisting of —H and —CH$_3$;
δ is the site of attachment to the anionic group;
L$_3$ is selected from a chemical bond, arenediyl, and a structure of Formula 13;

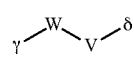

Formula 13 wherein:
γ is the site of attachment to the polymer backbone;
δ is the site of attachment to the anionic group;
W is selected from the structures in Formulas 14-20:

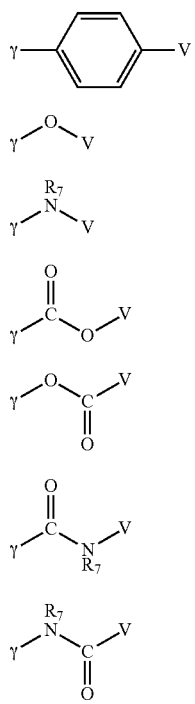

Formula 14

Formula 15

Formula 16

Formula 17

Formula 18

Formula 19

Formula 20 wherein:
R$_7$ is selected from the group consisting of —H and alkyl(ci-s); and
V is selected from the group consisting of alkanediyl, alkoxydiyl, alkylaminodiyl or alkenediyl;
R$_8$ is a chemical group resulting from polymer initiation; and
R$_9$ is a chemical group resulting chain termination.

In one embodiment of the polymer, R$_1$, and R$_2$ are independently selected from the group consisting of H, Na salt, and K salt. In one embodiment of the polymer, R$_1$, and R$_2$ are independently selected from the group consisting of H, Na salt, K salt, Zn salt, Ca salt, Sn salt, and amine cation salt.

In one embodiment of the polymer, R$_3$ is H. In another embodiment, R$_3$ is CH$_3$.

In one embodiment of the polymer, L$_1$ is a covalent bond. In another embodiment, L$_1$ has the structure of Formula 3. In another embodiment L$_1$ has the structure of Formula 3, the structure of X is selected from the group consisting of Formula 4, Formula 7 and Formula 9. In another embodiment, L$_1$ has the structure of Formula 3, X has the structure of Formula 4. In another embodiment, L$_1$ has the structure of Formula 3, X has the structure of Formula 7. In another embodiment, L$_1$ has the structure of Formula 3, X has the structure of Formula 9. In another embodiment, L$_1$ has the structure of Formula 3, X has the structure of Formula 5. In another embodiment, L$_1$ has the structure of Formula 3, X has the structure of Formula 4 and Y is alkanediyl. In another embodiment, L$_1$ has the structure of Formula 3, X has the structure of Formula 7 and Y is selected from the group consisting of alkanediyl and alkoxydiyl. In another embodiment, L$_1$ has the structure of Formula 3, X has the structure of of Formula 9 and Y is alkanediyl. In another embodiment, L$_1$ has the structure of Formula 3, X has the structure of Formula 5 and Y is alkanediyl.

In one embodiment of the polymer, said anionic group is selected from the group consisting of phosphate, phosphonate, sulfate, sulfonate or carboxylate. In another embodiment, said anionic group is sulfonate. In another embodiment, said anionic group is carboxylate. In another embodiment, said anionic group is phosphonate.

In one embodiment of the polymer, R$_5$ is H. In another embodiment, R$_5$ is CH$_3$. In another embodiment, L$_3$ is a covalent bond. In another embodiment, R$_5$ is H and L$_3$ is a covalent bond. In another embodiment, R$_5$ is CH$_3$ and L$_3$ is a covalent bond.

In one embodiment, L$_3$ has the structure of Formula 13 and W has the structure of Formula 14. In another embodiment, L$_3$ has the structure of Formula 13 and W has the structure of Formula 17. In another embodiment, L$_3$ has the structure of Formula 13 and W has the structure of Formula 19. In one embodiment, L$_3$ has the structure of Formula 13 and W has the structure of Formula 14 and V is alkanediyl. In another embodiment, L$_3$ has the structure of Formula 13 and W has the structure of Formula 17 and V is alkanediyl. In another embodiment, L$_3$ has the structure of Formula 13 and W has the structure of Formula 19 and V is alkanediyl.

In one embodiment of the compound, R$_8$, the chemical group resulting from polymer initiation, is selected from the structures of Formula 22-26:

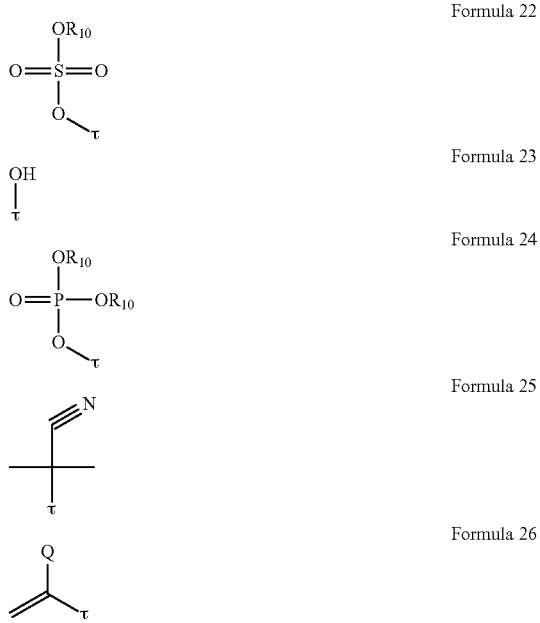

Formula 22

Formula 23

Formula 24

Formula 25

Formula 26 wherein:
R$_{10}$ is selected from the group consisting of —H, Na, K and amine cation salt;
τ is the site of attachment to polymer backbone and;
Q is the non-olefin residue of a monomer used in polymerization.

In a further embodiment, Q has the structure of Formula 27:

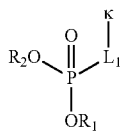

Formula 27 wherein: $L_1$, $R_1$ and $R_2$ are as previously noted and K denotes the site of attachment to Formula 26.

In a further embodiment, Q has the structure of Formula 28:

Formula 28 wherein: $L_3$, and δ are as previously note and K denotes the site of attachment to Formula 26.

In a further embodiment, Q is phosphonate. In a further embodiment Q is sulfonate.

In one embodiment of the compound, $R_9$, the chemical group resulting from polymer termination, is selected from the group consisting of —H. In one embodiment of the compound, $R_9$, the chemical group resulting from polymer termination, is another polymer chain with a head to head attachment.

In one preferred embodiment of the compound, $R_1$ and $R_2$, are independently selected from the group consisting of H, Na salt, K salt and amine cation salt, $R_3$ is H, $L_1$ is a covalent bond, $L_3$ is a covalent bond, the anionic group is sulfonate, $R_8$ is selected from the structures of Formula 22-26, Q is the structure of Formula 27 or Formula 28 and $R_9$ is H.

Methods of Making the Polymers and Resulting Structure

Embodiments of the present invention can be made using these general methods as follows.

The polymers of the present invention can be made by a wide variety of techniques, including bulk, solution, emulsion, or suspension polymerization. Polymerization methods and techniques for polymerization are described generally in Encyclopedia of Polymer Science and Technology, Interscience Publishers (New York), Vol. 7, pp. 361-431 (1967), and Kirk-Othmer Encyclopedia of Chemical Technology, 3rd edition, Vol 18, pp. 740-744, John Wiley & Sons (New York), 1982, both incorporated by reference herein. See also Sorenson, W. P. and Campbell, T. W., Preparative Methods of Polymer Chemistry. 2nd edition, Interscience Publishers (New York), 1968, pp. 248-251, incorporated by reference herein, for general reaction techniques suitable for the present invention. In one example, the polymers are made by free radical copolymerization, using water soluble initiators. Suitable free radical initiators include, but are not limited to, thermal initiators, redox couples, and photochemical initiators. Redox and photochemical initiators may be used for polymerization processes initiated at temperatures below about 30° C. Such initiators are described generally in Kirk-Othmer Encyclopedia of Chemical Technology, 3rd edition, John Wiley & Sons (New York), Vol. 13, pp. 355-373 (1981), incorporated by reference herein. Typical water soluble initiators that can provide radicals at 30° C. or below include redox couples, such as potassium persulfate/ silver nitrate, and ascorbic acid/hydrogen peroxide. In one example, the method utilizes thermal initiators in polymerization processes conducted above 40° C. Water soluble initiators that can provide radicals at 40° C. or higher can be used. These include, but are not limited to, hydrogen peroxide, ammonium persulfate, and 2,2'-azobis(2-amidinopropane) dihydrochloride. In one example, water soluble starting monomers are polymerized in a water at 60° C. using ammonium persulfate as the initiator.

The identity of chemical functional groups at the terminal ends of a linear polymer depend upon how the polymerization of that polymer chain was initiated and terminated. For free radical polymerization, any free radical in the system can begin a new chain. This free radical can be a direct derivative of the initiator such as a sulfate radical from persulfate, or alkyl radical from the azo type initiators (such as but not limited to 2,2'azobis(2-amidinopropane) dihydrochloride). The free radical can also be the result of a transfer reaction, for instance between a water and another radical to produce a hydroxyl radical or between a phosphate and another radical to produce a phosphate radical. Non-limiting examples of these resulting structures are given below, where R represents an H or appropriate counter ion such as Na, K or an amine and τ represents the site of attachment to the polymer.

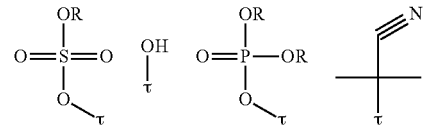

The free radical can also be the result of a chain transfer reaction, where the radical is transferred from a growing polymer chain to start a new chain. Chain transfer has been explicitly noted in polymerization of vinyl phosphonate monomers. Bingol et al. Macromolecules 2008, 41, 1634-1639), incorporated by reference herein, describe how polymerization of alkyl esters of vinyl phosphonate result in chain transfer on the alkyl group. This transfer ultimately begins a new polymer chain with an olefin containing chemical group on the initiating end.

Using the previously used nomenclature of using T to represent the site of attachment to the polymer, the initial functional group can be written as follows. It should be noted that this mechanism will produce a vinyl group with two protons on the same carbon atom.

The chemical group on the terminating end of the polymer chain depends upon how the chain is terminated. The most common terminations are the previously mentioned chain transfer, backbiting followed by beta scission, combination and disproportionation. In chain transfer and backbiting, the terminating group is typically a hydrogen. In combination, the propagating radicals on two chains react to form a new chain. This reaction causes a "head to head" configuration at the point of attachment.

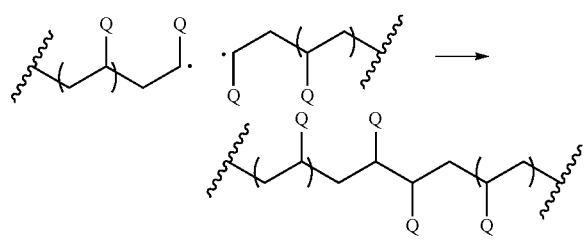

In disproportionation, a hydrogen is exchanged from one radical chain to another radical chain. The result is one chain is unsaturated while the other is saturated. Of note, the resulting unsaturated group is not a vinyl group. Each carbon in the unsaturation has only one hydrogen.

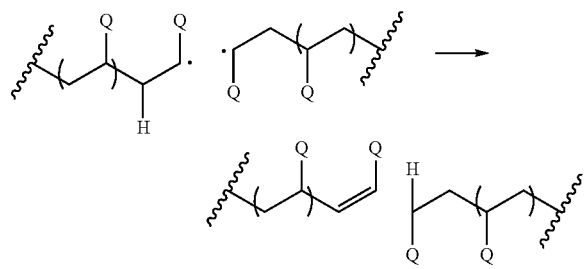

A polymer comprising a phosphonate group and anionic group can have the phosphonate and anionic groups attached directly off the polymer backbone, on a side group, or on a side chain. This phosphonate group can be incorporated into the polymer by either polymerization of monomers having the phosphonate group, or by polymerization of monomers without a phosphonate group and subsequent post-polymerization modification of the resulting polymer to add the phosphonate group. Similarly, the anionic group can be incorporated into the polymer by either polymerization of monomers having the anionic group, or by polymerization of monomers without an anionic group and subsequent post-polymerization modification of the resulting polymer to add the anionic group.

Uses of the Phosphonate Containing Polymers

The phosphonate and sulfonate containing polymers according to the present invention can be incorporated into a variety of compositions. These compositions include both aqueous and non-aqueous compositions. The compositions are useful for treating teeth and other oral care surfaces. In certain embodiments, the composition comprising phosphonate and sulfonate containing polymers is non-aqueous. In another embodiment, the composition is aqueous.

Oral Care Compositions

The present invention further relates to oral care compositions comprising the polymers of the present invention comprising a phosphonate group and anionic group. The oral care compositions of the present invention can further comprise additional ingredients such as polymeric mineral surface agent agents, metal ion salts, water, humectants, fluoride source, buffering agents, anticalculus agents, abrasive polishing materials, thickening agents, surfactants, titanium dioxide, colorants, flavorants, antimicrobial agents, and mixtures thereof.

A preferred polymeric mineral surface active agent is a polyphosphate. A polyphosphate is generally understood to consist of two or more phosphate molecules arranged primarily in a linear configuration, although some cyclic derivatives may be present. Although pyrophosphates are technically polyphosphates, the polyphosphates desired are those having around three or more phosphate molecules so that surface adsorption at effective concentrations produces sufficient non-bound phosphate functions, which enhance the anionic surface charge as well as hydrophilic character of the surfaces. The pyrophosphates are discussed separately under additional anticalculus agents. The inorganic polyphosphate salts desired include tripolyphosphate, tetrapolyphosphate and hexametaphosphate, among others. Polyphosphates larger than tetrapolyphosphate usually occur as amorphous glassy materials. Preferred in this invention are the linear "glassy" polyphosphates having the formula:

$$XO(XPO_3)_nX$$

wherein X is sodium or potassium and n averages from about 3 to about 125. Preferred polyphosphates are those having n averaging from about 6 to about 21, such as those manufactured by FMC Corporation and commercially known as Sodaphos (n≈6), Hexaphos (n≈13), and Glass H (n≈21). A particularly preferred polyphosphate has n averaging about 21 such as Glass H. These polyphosphates may be used alone or in a combination thereof.

Oral compositions which comprise polyphosphates are disclosed in e.g., U.S. Pat. Nos. 5,939,052, 6,190,644, 6,187,295, and 6,350,436, all assigned to The Procter & Gamble Co. In these compositions, the polyphosphates are disclosed to provide benefits including tartar inhibition and reducing aesthetic negatives such as astringency and staining caused by other actives such as stannous. The use of polyphosphates for the prevention of dental erosion is not disclosed. The polyphosphate sources are also described in more detail in Kirk-Othmer *Encyclopedia of Chemical Technology*, Fourth Edition, Volume 18, Wiley-Interscience Publishers (1996). An effective amount of a polymeric mineral surface active agent will typically be from about 1% to about 35%, preferably from about 2% to about 30%, more preferably from about 5% to about 25%, and most preferably from about 6% to about 20%, by weight of the total oral composition.

The metal ions suitable for use in the present invention have strong affinity for enamel surface and include stannous, copper and zinc ions. These ions provide surface protection effects by reacting with tooth surface ions and/or other components of the composition to produce highly insoluble compounds on the surface. Additionally, these metal ions undergo oxidation and hydrolysis under salivary pH conditions and produce insoluble deposits on tooth surfaces. The present compositions may comprise a metal ion source that provides stannous ions, zinc ions, copper ions, or mixtures thereof. The metal ion source can be a soluble or a sparingly soluble compound of stannous, zinc, or copper with inorganic or organic counter ions. Examples include the fluoride, chloride, chlorofluoride, acetate, hexafluorozirconate, sulfate, tartrate, gluconate, citrate, malate, glycinate, pyrophosphate, metaphosphate, oxalate, phosphate, carbonate salts and oxides of stannous, zinc, and copper. Preferred are stannous salts, such as stannous fluoride or stannous chloride.

Stannous, zinc and copper ions have been found to help in the reduction of gingivitis, plaque, sensitivity, and improved breath benefits. Dentifrices containing stannous salts, particularly stannous fluoride and stannous chloride, are described in U.S. Pat. No. 5,004,597 to Majeti et al. Other descriptions of stannous salts are found in U.S. Pat.

No. 5,578,293 issued to Prencipe et al. and in U.S. Pat. No. 5,281,410 issued to Lukacovic et al.

The combined metal ion source(s) will be present in an amount of from about 0.1% to about 11%, by weight of the final composition. Preferably, the metal ion sources are present in an amount of from about 0.5 to about 7%, more preferably from about 1% to about 5%. Preferably, the stannous salts may be present in an amount of from about 0.1 to about 7%, more preferably from about 1% to about 5%, and most preferably from about 1.5% to about 3% by weight of the total composition.

In preparing the present compositions, it is desirable to water and/or humectants to the compositions. Another optional component of the compositions desired herein is a humectant. The humectant serves to keep toothpaste compositions from hardening upon exposure to air and certain humectants can also impart desirable sweetness of flavor to toothpaste compositions. Suitable humectants for use in the invention include glycerin, sorbitol, polyethylene glycol, propylene glycol, and other edible polyhydric alcohols. The humectant generally comprises from about 0% to 70%, and preferably from about 15% to 55%, by weight of the composition.

Water will generally comprise from about 5% to about 70%, and preferably from about 10% to about 50%, by weight of the composition herein. Generally, the level of water is up to about 50%, preferably from about 5% to about 30%, and more preferably from about 10% to about 25%, by weight of the oral composition. The amounts of water include the free water which is added plus that which is introduced with other materials, such as with sorbitol, silica, surfactant solutions, and/or color solutions.

The oral composition of the present invention may incorporate a soluble fluoride source capable of providing free fluoride ions. The fluoride ion source may preferably be in a separate phase than the polymeric surface active agent to aid in stability. Preferred soluble fluoride ion sources include sodium fluoride, stannous fluoride, indium fluoride, amine fluoride and sodium monofluorophosphate. Sodium fluoride and stannous fluoride the most preferred soluble fluoride ion source. Stannous fluoride and methods of stabilization are described in U.S. Pat. No. 5,004,597 issued to Majeti et al. and in U.S. Pat. No. 5,578,293 issued to Prencipe et al., in addition to other sources Norris et al., U.S. Pat. No. 2,946,725, issued Jul. 26, 1960, and Widder et al., U.S. Pat. No. 3,678,154 issued Jul. 18, 1972, disclose such fluoride ion sources as well as others.

The present compositions may contain a buffering agent. Buffering agents, as used herein, refer to agents that can be used to adjust the pH of the compositions to a range of about pH 4 to about pH 10. The oral composition containing a polymeric mineral surface active agent will typically have a slurry pH of from about 4 to about 10, preferably from about 4.5 to about 8, and more preferably from about 5.5 to about 7. The buffering agents include alkali metal hydroxides, carbonates, sesquicarbonates, borates, silicates, phosphates, imidazole, and mixtures thereof. Specific buffering agents include monosodium phosphate, trisodium phosphate, sodium hydroxide, potassium hydroxide, alkali metal carbonate salts, sodium carbonate, imidazole, pyrophosphate salts, citric acid, and sodium citrate. Buffering agents are used at a level of from about 0.1% to about 30%, preferably from about 1% to about 10%, and more preferably from about 1.5% to about 3%, by weight of the present composition.

Pyrophosphate salts may be used in the present invention as anticalculus agents. The pyrophosphate salts useful in the present compositions include the dialkali metal pyrophosphate salts, tetra alkali metal pyrophosphate salts, and mixtures thereof. Disodium dihydrogen pyrophosphate ($Na_2H_2P_2O_7$), tetrasodium pyrophosphate ($Na_4P_2O_7$), and tetrapotassium pyrophosphate ($K_4P_2O_7$) in their unhydrated as well as hydrated forms are the preferred species. The amount of pyrophosphate salt useful in making these compositions is any tartar control effective amount, and is generally from about 1.5% to about 15%, preferably from about 2% to about 10%, and most preferably from about 2.5% to about 8%, by weight of the composition. The pyrophosphate salts are described in more detail in Kirk-Othmer *Encyclopedia of Chemical Technology*, Third Edition, Volume 17, Wiley-Interscience Publishers (1982).

An abrasive polishing material may also be included in the oral compositions. The abrasive polishing material contemplated for use in the compositions of the present invention can be any material which does not excessively abrade dentin. The abrasive polishing material should be formulated in the oral composition so that it does not compromise the stability of any ingredients, such as stannous fluoride. Typical abrasive polishing materials include silica gels and precipitates; aluminas; phosphates including orthophosphates, polymetaphosphates, and pyrophosphates; and mixtures thereof. Specific examples include dicalcium orthophosphate dihydrate, calcium pyrophosphate, tricalcium phosphate, calcium polymetaphosphate, insoluble sodium polymetaphosphate, hydrated alumina, beta calcium pyrophosphate, calcium carbonate, and resinous abrasive materials such as particulate condensation products of urea and formaldehyde, and others such as disclosed by Cooley et al in U.S. Pat. No. 3,070,510, issued Dec. 25, 1962. Mixtures of abrasives may also be used. Silica dental abrasives of various types are preferred because of their unique benefits of exceptional dental cleaning and polishing performance without unduly abrading tooth enamel or dentine. The abrasive in the toothpaste compositions described herein is generally present at a level of from about 6% to about 70% by weight of the composition. Preferably, toothpastes contain from about 10% to about 50% of abrasive, by weight of the dentifrice composition.

The present invention may also include an alkali metal bicarbonate salt. Alkali metal bicarbonate salts are soluble in water and unless stabilized, tend to release carbon dioxide in an aqueous system. Sodium bicarbonate, also known as baking soda, is the preferred alkali metal bicarbonate salt. The alkali metal bicarbonate salt also functions as a buffering agent. The present composition may contain from about 0.5% to about 50%, preferably from about 0.5% to about 30%, more preferably from about 2% to about 20%, and most preferably from about 5% to about 18% of an alkali metal bicarbonate salt, by weight of the dentifrice composition.

The present invention provides compositions in the form of toothpastes, dentifrices, tooth powder, topical oral gels, mouthrinses, denture product, mouthsprays, lozenges, oral tablets, and chewing gums. Typically these compositions will contain some thickening material or binders to provide a desirable consistency. Preferred thickening agents are carboxyvinyl polymers, carrageenan, hydroxyethyl cellulose, and water soluble salts of cellulose ethers such as sodium carboxymethylcellulose and sodium hydroxyethyl cellulose. Natural gums such as gum karaya, xanthan gum, gum arabic, and gum tragacanth can also be used. Colloidal magnesium aluminum silicate or finely divided silica can be used as part of the thickening agent to further improve texture. Thickening agents can be used in an of amount from about 0.1% to about 15%, by weight of the dentifrice composition.

The present compositions may also comprise surfactants, also commonly referred to as sudsing agents. Suitable surfactants are those which are reasonably stable and foam throughout a wide pH range. The surfactant may be anionic, nonionic, amphoteric, zwitterionic, cationic, or mixtures thereof. Anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate and sodium coconut monoglyceride sulfonates are examples of anionic surfactants of this type. Other suitable anionic surfactants are sarcosinates, such as sodium lauroyl sarcosinate, taurates, sodium lauryl sulfoacetate, sodium lauroyl isethionate, sodium laureth carboxylate, and sodium dodecyl benzenesulfonate. Mixtures of anionic surfactants can also be employed. Many suitable anionic surfactants are disclosed by Agricola et al., U.S. Pat. No. 3,959,458, issued May 25, 1976. Nonionic surfactants which can be used in the compositions of the present invention can be broadly defined as compounds produced by the condensation of alkylene oxide groups (hydrophilic in nature) with an organic hydrophobic compound which may be aliphatic or alkyl-aromatic in nature. Examples of suitable nonionic surfactants include poloxamers (sold under trade name Pluronic), polyoxyethylene, polyoxyethylene sorbitan esters (sold under trade name Tweens), fatty alcohol ethoxylates, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides, and mixtures of such materials. The amphoteric surfactants useful in the present invention can be broadly described as derivatives of aliphatic secondary and tertiary amines in which the aliphatic radical can be a straight chain or branched and wherein one of the aliphatic substituents contains from about 8 to about 18 carbon atoms and one contains an anionic water-solubilizing group, e.g., carboxylate, sulfonate, sulfate, phosphate, or phosphonate. Other suitable amphoteric surfactants are betaines, specifically cocamidopropyl betaine. Mixtures of amphoteric surfactants can also be employed. Many of these suitable nonionic and amphoteric surfactants are disclosed by Gieske et al., U.S. Pat. No. 4,051,234, issued Sep. 27, 1977. The present composition typically comprises one or more surfactants each at a level of from about 0.25% to about 12%, preferably from about 0.5% to about 8%, and most preferably from about 1% to about 6%, by weight of the composition.

Titanium dioxide may also be added to the present composition. Titanium dioxide is a white powder which adds opacity to the compositions. Titanium dioxide generally comprises from about 0.25% to about 5%, by weight of the composition.

Coloring agents may also be added to the present composition. The coloring agent may be in the form of an aqueous solution, preferably 1% coloring agent in a solution of water. Color solutions generally comprise from about 0.01% to about 5%, by weight of the composition.

A flavor system can also be added to the compositions. Suitable flavoring components include oil of wintergreen, oil of peppermint, oil of spearmint, clove bud oil, menthol, anethole, methyl salicylate, eucalyptol, cassia, 1-menthyl acetate, sage, eugenol, parsley oil, oxanone, alpha-irisone, marjoram, lemon, orange, propenyl guaethol, cinnamon, vanillin, ethyl vanillin, heliotropine, 4-cis-heptenal, diacetyl, methyl-para-tert-butyl phenyl acetate, xylitol, and mixtures thereof. Coolants may also be part of the flavor system. Preferred coolants in the present compositions are the paramenthan carboxyamide agents such as N-ethyl-p-menthan-3-carboxamide (known commercially as "WS-3") and mixtures thereof. A flavor system is generally used in the compositions at levels of from about 0.001% to about 5%, by weight of the composition.

The present invention may also include other agents, such as antimicrobial agents. These agents may be present at levels of from about 0.01% to about 1.5%, by weight of the dentifrice composition.

The oral compositions of the present invention are in the form of toothpastes, dentifrices, topical oral gels, mouthrinses, denture products, mouthsprays, lozenges, oral tablets, or chewing gums. The dentifrice compositions may be a paste, gel, or any configuration or combination thereof.

EXAMPLES

The following examples further describe and demonstrate the preferred embodiments within the scope of the present invention. The examples are given solely for the purpose of illustration and are not to be construed as limitations of the present invention since many variations thereof are possible without departing from the spirit and scope of the invention. Ingredients are identified by chemical name, or otherwise defined below.

Powder Stain Prevention Model (PSPM)

The Powder Stain Prevention Model (PSPM) is a screening technique where hydroxyapatite powder (HAP) is used as a substrate for stain accumulation. The general purpose of this technique is to illustrate and quantify the stain prevention ability or staining potential of chemical agents used in oral care. Hydroxyapatite powder provides a large surface area to which tea chromogens adsorb. Pretreatment of HAP with oral care actives, either in rinse or dentifrice form, results in different levels of stain accumulation depending upon the ability of the actives to block or enhance the binding of these chromogens onto HAP surface. The magnitude of stain can then be quantified by image analysis. Steps involved in PSPM are described below.

1. HAP Pretreatment

Measure 200 mg-210 mg of HAP powder (BioGel® HTP-Gel Catalog #130-0421, Bio-Rad Laboratories (Hercules, Calif.) into 50 ml centrifuge tubes. Add 20 ml of treatment to each tube. For simple polymer the treatment is a 2 wt % of polymer or control at 100% active basis used. For dentifrice formulations, weigh 8 g of each of the toothpaste into labeled 50 g round bottom centrifuge tubes. Add 24 g of deionized water into the tubes (so that the slurry ratio is 1:3). Vortex for 1 min to mix well to prepare the slurry with no chunks of toothpaste. Centrifuge the slurry for 15 min at 15,000 rpm using the centrifuge and use 20 mL of supernantent as the treatment. Tube is vortexed for 30 seconds to fully suspend HAP in treatment followed by centrifugation at 15,000 rpm for 15 mins. After centrifugation, supernatant is decanted and pellet redistributed by adding 25 ml of water, vortexing, centrifuging at 15,000 rpm for 15 mins, and decanting—making sure pellet breaks up during vortexing. The wash cycle is repeated two more times.

2. HAP Staining

After final water wash, 20 ml of filtered tea (1 Lipton tea bag per 100 ml of hot water seeped for 5 minutes, filtered and used at 50° C.) is added to each pellet and vortexed for 30 seconds to fully suspend HAP in tea. Powder suspension is centrifuged at 15,000 rpm for 15 mins and decanted. About 25 ml of water is added to the tube, vortexed and then centrifuging at 15,000 rpm for 15 mins. The liquid is decanted and wash cycle is repeated 2 more times.

3. HAP Prep for Color Analysis

Vortex pellet in approximately 10 ml of water until fully suspended followed by filtering under vacuum onto a Millipore filter disk (Membrane Filters 4.5 tm, 47 mm Catalog #HAWPO4700, Millipore Corporation, Bedford, Mass.). Prepare a control disk using. −200 mg of untreated, unstained HAP. Filter disks are then dried overnight in flat position and then laminated.

4. Color Analysis of Stained HAP

Whitelight system: HAP disk (untreated HAP control and HAP treatments) is placed in a stabilized sample holder. The color is measured using a digital camera having a lens equipped with a polarizer filter (Camera model no. CANON EOS 70D from Canon Inc., Melville, NY with NIKON 55 mm micro-NIKKOR lens with adapter). The light system is provided by Dedo lights (model number DLH2) equipped with 150 watt, 24V bulbs model number (Xenophot model number HL X64640), positioned about 30 cm apart (measured from the center of the external circular surface of one of the glass lens through which the light exits to the other) and aimed at a 45 degree angle such that the light paths meet on the HAP disk. Image analysis is performed using Whitelight with Ultragrab, Optimas and Giant Imaging software.

5. Controls

Usual controls for a single polymer PSPM are water as a treatment followed by exposure to tea, and water without exposure to tea. Additionally, pyrophosphate and polyphosphate are run as internal controls.

6. Results

Calculate changes in L*(brightness), a*(red(+)/green(−)), b*(yellow (−)/blue(+)), and in E (total color) as follows:

$$\Delta L = L^*_{untreated\ HAP} - L^*_{treated\ HAP}$$

$$\Delta a = a^*_{untreated\ HAP} - a^*_{treated\ HAP}$$

$$\Delta b = b^*_{untreated\ HAP} - b^*_{treated\ HAP}$$

$$\Delta E = (\Delta L)^2 + (\Delta a)^2 + (\Delta b)^2$$

Report results as average ΔL, Δa, Δb, and/or ΔE and percent prevention of stain (AL & AE) versus the negative control.

Powder Stain Removal Model (PSRM)

The Powder Stain Removal Model (PSRM) is a screening technique where hydroxyapatite powder (HAP) is used as a substrate for stain accumulation. The purpose of this technique is to illustrate and quantify the stain removal properties of chemical agents used in oral care. Hydroxyapatite powder provides a large surface area to which tea chromogens adsorb. Treatment of stained HAP with oral care actives, either in rinse or dentifrice form, results in different levels of stain removal depending upon the ability of the actives to disrupt the binding of these chromogens onto HAP surface. The magnitude of stain removal can then be quantified by image analysis. A trial of this model can be completed in three days. Steps involved in PSRM are described below.

1. HAP Staining

Prepare large batch of tea stain HAP by stirring 10 g of HAP powder in 200 ml of filtered tea for 5 minutes. Divide into centrifuge tubes and centrifuge at 15,000 rpm for 15 mins. Wash pellet by adding in 25 ml of water, vortexing, centrifuging at 15,000 rpm for 15 mins, and pipet out liquid. Make sure pellet breaks up during vortexing. Repeat wash.

Place centrifuge tubes in convection oven (55-65° C.) overnight to dry stained HAP. Once dried, pool stained HAP together and grind to a fine powder with pestle and mortar.

2. HAP Treatment

Measure 200 mg-210 mg of HAP powder (BioGel® HTP-Gel Catalog #130-0421, Bio-Rad Laboratories (Hercules, Calif.) into 50 ml centrifuge tubes. Add 20 ml of treatment to each tube. For simple polymer the treatment is a 2 wt % of polymer or control at 100% active basis used. For dentrifice formulations, weigh 8 g of each of the toothpaste into labeled 50 g round bottom centrifuge tubes. Add 24 g of deionized water into the tubes (so that the slurry ratio is 1:3). Vortex for 1 min to mix well to prepare the slurry with no chunks of toothpaste. Centrifuge the slurry for 15 min at 15,000 rpm using the centrifuge and use 20 mL of supernantent as the treatment. Tube is vortexed for 1 minute to fully suspend HAP in treatment followed by centrifugation at 15,000 rpm for 15 mins. After centrifugation, supernatant is decanted and pellet redistributed by adding 25 ml of water, vortexing, centrifuging at 15,000 rpm for 15 mins, and decanting—making sure pellet breaks up during vortexing. The wash cycle is repeated one more time.

3. HAP Prep for Color Analysis

Vortex pellet in approximately 10 ml of water until fully suspended followed by filtering under vacuum onto a Millipore filter disk (Membrane Filters 4.5 tm, 47 mm Catalog #HAWP04700, Millipore Corporation, Bedford, Mass.). Prepare a control disk using ≈200 mg of untreated, stained HAP. Filter disks are then dried overnight in flat position and then laminated.

4. Color Analysis of Stained HAP

Whitelight system: HAP disk (untreated HAP control and HAP treatments) is placed in a stabilized sample holder. The color is measured using a digital camera camera having a lens equipped with a polarizer filter (Camera model no. CANON EOS 70D from Canon Inc., Melville, NY with NIKON 55 mm micro-NIKKOR lens with adapter). The light system is provided by Dedo lights (model number DLH2) equipped with 150 watt, 24V bulbs model number (Xenophot model number HL X64640), positioned about 30 cm apart (measured from the center of the external circular surface of one of the glass lens through which the light exits to the other) and aimed at a 45 degree angle such that the light paths meet on the HAP disk. Image analysis is performed using Whitelight with Ultragrab, Optimas and Giant Imaging software.

5. Controls

Usual controls for a single polymer PSRM are water as a treatment followed by exposure to tea, and water without exposure to tea. Additionally, pyrophosphate and polyphosphate are run as internal controls.

6. Results

Calculate changes in L*(brightness), a*(red(+)/green(−)), b*(yellow (−)/blue(+)), and in E (total color) as follows:

$$\Delta L = L^*_{treated\ HAP} - L^*_{untreated\ HAP}$$

$$\Delta a = a^*_{treated\ HAP} - a^*_{untreated\ HAP}$$

$$\Delta b = b^*_{treated\ HAP} - b^*_{untreated\ HAP}$$

$$\Delta E = \sqrt{(\Delta L)^2 + (\Delta a)^2 + (\Delta b)^2}$$

Report results as average ΔL, Δa, Δb, and/or ΔE and percent prevention of stain (AL & AE) versus the negative control.

In-Vitro Pellicle Tea Stain Model (iPTSM)

Tooth staining is a common undesirable side effect of the use of stannous fluoride compositions. Improved stannous fluoride dentifrices described herein provide reduced dental stain formation resulting from more efficient stannous delivery from stannous bound to the polymeric mineral surface active agent. The staining of the tooth surface typically caused by stannous is measured in the clinical situation by using a stain index such as the Lobene or Meckel indices described in the literature. For rapid screening of technologies to help mitigate stannous induced staining, an in vitro lab method is used that provides quantitative estimates of stain prevention potential of stannous fluoride formulations. This method, called iPTSM (in-vitro pellicle stain model), has been shown to correlates well with clinical observations. The in vitro pellicle tea stain model (iPTSM) is a technique where an in vitro plaque biomass is grown on glass rods from pooled human stimulated saliva over the course of three days. The plaque biomass is treated with agents to determine potential dental staining levels of the various agents. The purpose of this technique is to provide a simple and quick method for determining if compounds have a direct effect on the amount of dental plaque stain. This method utilizes plaque grown on polished glass rods from pooled human saliva with treatments of 5 minutes duration, followed by a 10 minute tea treatment. A trial of this in vitro model can be completed in five days during which up to 12 treatments, including controls can be evaluated.

1. Roughening Glass Rods

Polish new glass rods (5 mm×90 mm) approximately 25 mm from the untapered end on a lathe with silicon carbide paper of 240, 320, 400, and 600 grit used sequentially. After the initial polishing, polish the rods with 600 grit paper only before each test.

2. Saliva Collection & Preparation

Collect saliva daily from a panel of 5-10 people by paraffin stimulation and refrigerate at 4° C. till needed. Pool saliva carefully (so not to pour in wax/mucus) and mix thoroughly.

3. Day 1: Clean glass rods by sonicating with dilute HCl acid, rinse, dry, and polish with 600 grit silicon carbide paper. Rinse rods again with DI water and dry. Insert rods into holders, adjust depth with the depth gauge on the treatment rack, and secure rods in place with rubber O-rings. In the early afternoon, pipette 7 ml of saliva, to which 0.1 wt % sucrose has been added, into 16×75 mm test tubes in a dipping rack. Sucrose is added to saliva on the first day only. Place the rod holders in a modified 37° C. incubator designed to dip roughened glass rods into test tubes to a depth of 1.5 cm at 1 rpm. Dip rods overnight. The design of the incubator is fully shown in Attachment 1. Prepare plaque growth media described above and autoclave for Day 2 (saliva is added on Day 2 before use).

4. Day 2: In the morning, add saliva to plaque growth media and mix thoroughly. Pipette 7 ml of plaque growth media into new 16/75 mm test tubes in new dipping rack. Remove old rack of used tubes, place new dipping rack into incubator, and dip rods for six hours MINIMUM before replacing rods into fresh saliva for overnight dipping.

5. Day 3: On the morning of the third day, pipette 10 ml of DI water into 17×100 mm test tubes in the second and third rows of the treatment rack. This applies to dentifrice treatments only. Rinse solutions may or may not have water rinse tubes in the treatment rack. Pipette fresh pooled saliva into a dipping rack and set aside. Begin tea preparation by adding 550 ml to a glass beaker and heating it in the microwave for 10 minutes. At the end of ten minutes, carefully remove beaker from microwave and drop in a magnetic stir bar to dissipate the possible presence of a super-heated water core. Place 5 Lipton tea bags and a Celsius thermometer into the water and stir on a hot plate. This solution needs to be monitored to insure that it will be no hotter than 50° C. when tea treatment begins. While tea treatment is heated and mixed, prepare dentifrice slurries (1 part dentifrice to 3 parts water, also called a 1 in 4 dilution) using a handheld homogenizer for 30 seconds. Centrifuge slurries for 15 minutes at 10000 rpm. Rinse or active solutions are treated neat. Pipette 7 ml of 50° C. tea solution into a separate dipping rack. Add 5 ml of supernatant/rinse to 16×75 mm glass test tubes in the first row of the treatment rack. Turn off incubator dipping mechanics and remove old saliva dipping rack. Remove all rod holders from the incubator and place submerged rods into old saliva dipping rack to prevent drying over. Using one rod holder at a time, treats by soaking for 5 minutes in the treatment rack. If applicable, wash rods with 2×10 sec dipping in the test tubes containing the DI water in the treatment rack. Place rod holders into prepared tea solution dipping rack and soak for 10 min. Repeat this process with all four rod holders, returning holders to dipping rack to prevent drying out. Place fresh saliva dipping rack into incubator. Return rods to the incubator after treatment/tea soak and dip in fresh saliva for at MINIMUM of 1 hour. This treatment cycle is repeated two more times with fresh treatment/tea/saliva solutions for a total of 3 treatments in a day. After the last treatment, return rods to the incubator and dip overnight in fresh saliva.

6. Day 4: On the morning of the fourth day, turn off incubator dipping mechanics and remove rods from the saliva. Allow rods to dry are then weigh to the nearest 0.1 mg. Record weight and calculate mean dry plaque biomass weights and standard deviations. Place rods into clean sterile cap-able test tubes containing 3 ml of 0.5M KOH, cap tightly and digest overnight at 37° C.

7. Day 5: On the fifth day, remove rods from the incubator and allow cooling. Vortex glass rods to insure all deposits are homogenized. Remove rods from test tubes, filter the solution through 0.45 μm cellulose acetate syringe filters and an read absorbance values for each rod at 380 nm in spectrophotometer. Record results and use absorbance values to calculate mean absorbance value per treatment, standard deviations per treatment, mean absorbance per mg plaque, Standard deviations of mean absorbance per mg plaque, and % increase in absorbance per mg plaque vs. control according to the following equation, % Stain Potential=((Test Product Abs/biomass−Non stannous control Abs/Biomass)/(High Stannous control Abs/Biomass−Non stannous control Abs/Biomass))*100

Example 1 Co-Polymerization of Vinyl Phosphonic Acid (VPA) and Sodium Vinyl Sulfonate (SVS)

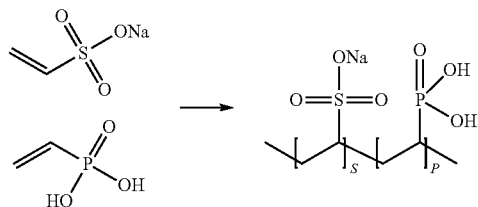

VPA (2.0 g, 18.5 mmoles) and SVS (25% aqueous solution, 7.9 g, 15.2 mmoles), initial molar ratio of SVS to VPA of 45 to 55, were charged in a round bottom flask. The flask was purged with nitrogen for 15 minutes and heated to 90° C. Two separate aqueous solutions containing 2,2'-azobis(2-methylpropionamidine) dihydrochloride (AAPH, Aldrich, 25.8 mg in 1.2 mL water, 0.3% molar basis to total monomers added) and 1-Octanethiol (CTA, Aldrich 55.6 mg in 1.2 mL of water, 1.1% molar basis to total monomers added) were also prepared. These two solutions were then added to the heated stirred flask containing the monomers every 30 minutes over the course of 6 hours. After the final addition, the resulting solution was allowed to stir overnight at 90° C. $^1$H-NMR & $^{31}$P-NMR were run on the crude reaction solutions. Typical monomer conversions of 95-99% were observed with a broad P polymer peak at −31 ppm from the phosphonate group. The crude reaction solutions were diluted to 1 wt % polymer in water and the pH adjusted to 6. These solutions were dialyzed with 2K molecular weight cut off dialysis membranes against reverse osmosis water for 5-7 days.

The resultant solution was stripped of water under vacuum to yield white to cream color solids which was further dried in a vacuum oven overnight to yield 2.74 g of solid.

The phosphonate content in the polymers were determined by preparing an NMR sample with purified polymer & trimethyl phosphate (TMP) in D$_2$O. The $^1$H & $^{31}$P-NMR's were run from which the phosphonate content was calculated from the H and P peaks of the internal standard (TMP) relative to the polymer peaks and water. Based on this analysis, the polymer contained 55.7 mol % repeat units resulting from SVS and 44.3 mol % repeat units resulting from VPA. The water content was calculated to 9.6% on a weight basis. The total recovery of monomers in the post dialysis polymer was calculated to be 57% on a molar basis.

Example 2 Co-Polymerizations of Vinyl Phosphonic Acid and Sodium Vinyl Sulfonate (SVS)

The procedure of Example 1 was repeated for different starting ratios of VSA and VPA. The resulting polymer compositions from different starting ratios and total yield, including Example 1 are shown in the Table 1 below. A Wyatt Gel Permeation Chromatography (GPC) system, using a Polymer Standards Service (PSS) MCX 1000A column and both a Wyatt HELEOS II light scattering detector and a Wyatt Optilab Differential refractive index detector, was used for calculation of polymer molecular weight using the internal Wyatt Astra 6 software.

TABLE 1

| % Total Monomer SVS Loaded | % Total Monomer VPA Loaded | % AAPH Loaded | % CTA Loaded | % Sulfonate in Polymer | % Phosphonate in Polymer | Total Molar Yield | Mn (kDa) | Mw (kDa) |
|---|---|---|---|---|---|---|---|---|
| 75.0% | 25.0% | 0.3% | 1.0% | 80% | 20% | 85% | 5.4 | 7.9 |
| 70.0% | 30.0% | 0.3% | 1.1% | 69% | 31% | 66% | 4.2 | 5.9 |
| 50.0% | 50.0% | 0.3% | 1.0% | 57% | 43% | 73% | — | — |
| 45.1% | 54.9% | 0.3% | 1.1% | 56% | 44% | 57% | 3.4 | 4.5 |
| 40.0% | 60.0% | 0.3% | 1.0% | 44% | 56% | 64% | 4.2 | 5.3 |
| 20.0% | 80.0% | 0.3% | 1.0% | 34% | 66% | 58% | — | — |

Example 3 PSPM on VPA SVS Co Polymers

The polymers from Example 2 were tested according the PSPM model along with homopolymers of Poly Vinyl Sulfonate and Poly Vinyl phosphonate purchased from Poly-Sciences Inc. Results are shown in FIG. 1 and Table 2 (below) along with pyrophosphate and polyphosphate.

TABLE 2

| Source/Name | % S | % P | Delta L |
|---|---|---|---|
| PolyScience | 100% | 0% | 16.3 |
| Example 2 | 80% | 20% | 8.7 |
| Example 2 | 69% | 31% | 9.0 |
| Example 2 | 57% | 43% | 6.0 |
| Example 2 | 56% | 44% | 6.7 |
| Example 2 | 44% | 56% | 9.3 |
| Example 2 | 34% | 66% | 12.9 |
| PolyScience | 0% | 100% | 15.8 |
| Pyrophosphate | | | 16.3 |
| Polyphosphate | | | 2.0 |

Example 4 PSRM on VPA SVS Co Polymers

Figure 2:
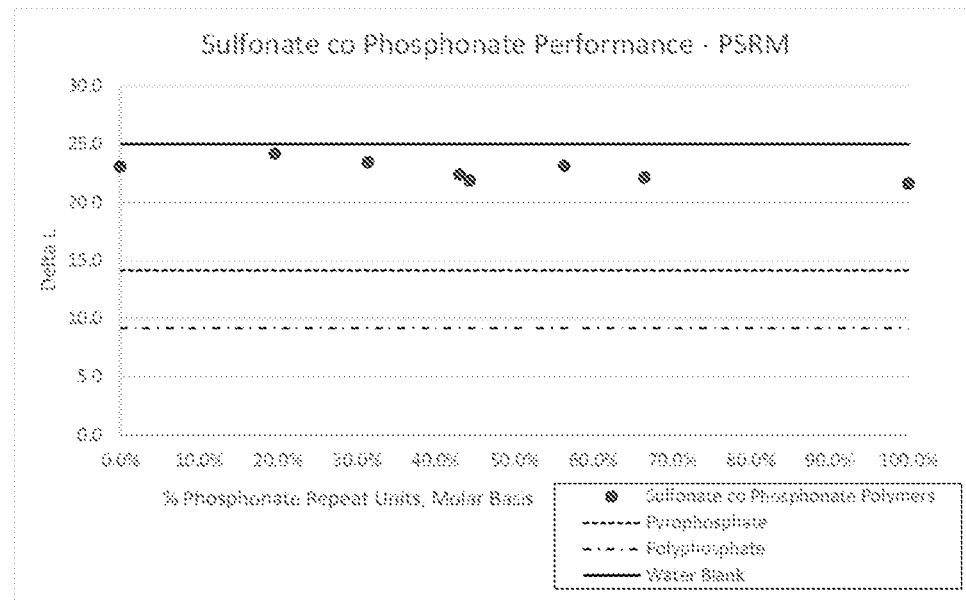
FIG. 2 is a chart showing polymer performance.

The polymers from Example 2 were tested according the PSRM model along with homopolymers of Poly Vinyl Sulfonate and Poly Vinyl phosphonate purchased from Poly-Sciences Inc. Results are shown in FIG. 2 and Table 3 (below) along with pyrophosphate, polyphosphate and the water treatment.

TABLE 3

| Source/Name | % Sulfonate in Polymer | % Phosphonate in Polymer | Delta L |
|---|---|---|---|
| PolyScience | 100.0% | 0% | 23.1 |
| Example 2 | 80% | 20% | 24.2 |
| Example 2 | 69% | 31% | 23.5 |
| Example 2 | 57% | 43% | 22.4 |
| Example 2 | 56% | 44% | 21.9 |
| Example 2 | 44% | 56% | 23.2 |
| Example 2 | 34% | 66% | 22.2 |
| PolyScience | 0.0% | 100% | 21.6 |
| Pyrophosphate | | | 14.2 |
| Polyphosphate | | | 9.2 |
| Water Blank | | | 25.0 |

Example 5—20-30 g Scale Up of Example 1 and 2

The procedure of Examples 1 and 2 was scaled up using 148 mmoles of VPP and 122 mmoles of VSA with an equivalent increase of other reagents and solvents. After dialysis and freeze drying, 26.8 g of polymer was collected and found to contain 54% monomers based on SVS, 46% based on VPA. The polymer was 90% active on a weight basis with 10% impurities/water. This polymer was tested in the PSPM and PSRM models with values of ΔL of 10.2 and 20.2 respectively. The controls for the PSPM were: Water 28.0, HAP Blank 0.0, Pyrophosphate 14.3, Polyphosphate 3.1, and the controls for the PSRM were: Water 25.0, HAP Blank 0.0, Pyrophosphate 13.5, Polyphosphate 10.7.

Example 6—Formulation and Testing of Example 5

The polymer from Example 5 was tested in a dentrifice formulations. The composition of this formulation, and the relative controls are shown in TABLE 4. PSRM, PSPM, and iPTSM were conducted on the formulations and the data from these tests is included in Table 4 as well. All percentages in this example are by weight unless otherwise noted. The compositions were prepared as follows:
Composition #1 was commercially purchased Crest Cavity Protection Regular Flavor.
Composition #2 was commercially purchased Crest Pro-Health Clean Mint Smooth Formula.
Composition #3 is the same as Composition #2 with the addition of Polymer Example 5.
Composition #2 was weighed into a Speedmix jar. The polymer Example 5 was then added to the Speedmix jar and mixed in a Speedmixer until homogeneous. The pH was then determined with a pH electrode and 50% NaOH solution was added and mixed in a Speedmixer to adjust the pH to a target of ~6.
Composition #4 was prepared in a pilot scale mixer by adding approximately half of the sorbitol to the mixer, heating to 65° C. with a heating/cooling jacket on the tank and pulling vacuum. Ina separate container 1 weight percent of the silica and all the hydroxyethyl cellulose were dry blended until homogeneous and then drawn by vacuum into the mixing vessel. A both an anchor agitator and high shear rotor/stator device were used to mix and homogenize the mixture to assure homogeneity and hydration of the hydroxyethyl cellulose. Once homogeneous, the rotor/stator device was turned off. The remaining sorbitol, about 25% of the water and all the blue dye were added and mixed until homogeneous using the anchor agitator. In a separate container, 1 weight percent of the silica, all the saccharin and all the carrageenan were dry blended and drawn into the main mix vessel under vacuum with the high shear rotor/stator device and anchor agitator running. Once homogenous, the rotor/stator was turned off. Next the remaining silica was drawn into the main mix vessel under vacuum and mixed using the anchor agitator at a vacuum not less than 26 inches of mercury. The batch was then cooled to approximately 49° C. via the heating/cooling jacket while continuing to be mixed with the anchor agitator. Once the batch reached 49° C., the anchor agitator was stopped, the mixer was opened and the flavor and sodium lauryl sulfate solution were added to the top of the batch. Vacuum was then pulled to 24 inches of mercury and the anchor agitator and rotor/stator were turned on until the batch was homogeneously mixed. After mixing, the rotor/stator was turned off and vacuum was pulled to 27 inches of mercury to remove air. In a separate container, the remaining 75% of the water was heated to 65C. Sodium gluconate was added to the water and mixed until dissolved. Stannous fluoride was then added to the gluconate solution and mixed until dissolved. Stannous chloride was then added to the gluconate solution and mixed until dissolved. Once this solution was prepared, it was added under vacuum to the main mix vessel and mixed using the anchor agitator until homogeneous. After the mixing, the sodium hydroxide was added under vacuum to the main mix vessel and the anchor agitator and rotor/stator were used to mix homogeneously. Once homogeneous, the rotor/stator was turned off and the heating/cooling jacket was reduced to 30° C. and vacuum was pulled to 26 inches of mercury. The batch was mixed under vacuum until the temperature reached 35° C., it was pumped out of the main mix vessel.

TABLE 4

|  | Composition #1 iPTSM Negative Control | Composition #2 Formula #1 Nil Polymer | Composition #3 Formula #1 w/Example 5 | Composition #4 Formula #2 Nil Polymer (iPTSM Positive Control) |
|---|---|---|---|---|
| H2O | 11.165 | 21.156 | 20.719 | 13 |
| NaF | 0.243 | | | |
| SnF2 | | 0.454 | 0.445 | 0.454 |
| NaOH (50%) | | 0.87 | 0.881 | 0.8 |
| Sorbitol | 65.508 | 48 | 47.009 | 55.159 |
| Monosodium Phosphate dihydrate | 0.419 | | | |
| Trisodium Phosphate Dodecahydrate | 1.1 | | | |
| Carboxy Methyl Cellulose | 0.75 | | | |
| Carbomer 956 | 0.3 | | | |
| Z119 | 15 | 0.056 | 0.055 | 20 |
| Z109 | | 17.5 | 17.139 | 0 |
| TiO2 | 0.525 | 0.5 | 0.49 | 0.25 |
| Carrageenan | | 1.5 | 1.469 | 0.8 |
| Xanthan Gum | | 0.875 | 0.857 | 0 |
| Hydroxyethyl Cellulose | | 0 | | 0.5 |
| Sodium Lauryl Sulfate (29% Sol'n) | 4 | 5.00 | 4.897 | 4 |
| Saccharin | 0.13 | 0.45 | 0.441 | 0.455 |
| Flavor | 0.81 | 1.30 | 1.273 | 1 |
| ZnCitrate | | 0.53 | 0.522 | 0 |
| NaGluconate | | 1.30 | 1.273 | 2.082 |
| SnCl2*2H2O | | 0.51 | 0.495 | 1.5 |
| 2N HCl | | 0.28 | 0 | |
| Dye Solution | 0.05 | | | |
| Example 54 (VSA/VPP) | | 2.35 | 0 | |
| Example 55 (VSA/VPA) | | 0 | 2.036 | |
| Example 56 (VSA/VPP) | | | 0 | |
| Total | 100 | 100 | 100 | 100 |
| PSPM (ΔL/ ΔE) | 24.3/31.07 | 19.47/ 27.84 | 12.62/ 18.10 | 30.91/ 43.91 |
| PSRM (ΔL/ ΔE) | 19.47/24.72 | 18.15/ 24.55 | 16.96/ 22.71 | 21.02/ 30.71 |
| iPTSM % Stain Potential | 0% | 3% | -49% | 100% |

Example 7—Synthesis of Polymer Containing VPA and VSA Residues from Methyl Phosphonate

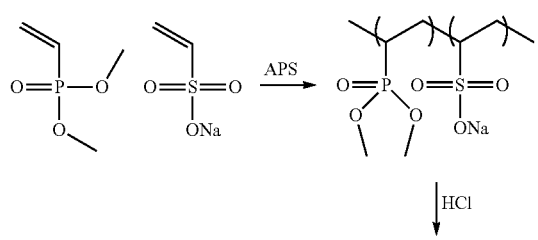

-continued

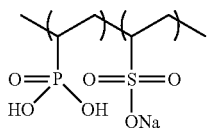

Dimethyl vinyl phosphonate, DMVP (10.6 g, 77.9 mmoles) and sodium vinyl sulfonate solution, SVS (25% aqueous solution, 40.5 g, 77.9 mmoles), were charged in a 100 mL round bottom flask. The flask was purged with nitrogen for 15 minutes and heated to 60° C. Ammonium persulfate APS, 888 mg, 2.55% of total monomer, was brought up in 4 g of water and degassed with nitrogen for 5 minutes. The APS solution was added to the solution containing DMVP and SVS and resultant solution was allowed to stir for 24 hours under nitrogen at 60° C.
$^1$H-NMR & $^{31}$P-NMR were run on the crude reaction solution, and a monomer conversion of around 99% was observed with a broad P polymer peak at ~37 ppm from the phosphonate group. The crude reaction solution was diluted to 10 wt % polymer in water with 207 g of water. To this was added 300 mL of acetone over 30 minutes under continuous stirring at room temperature to yield a turbid solution. After standing in a separatory funnel for 30 minutes a lower viscous polymer rich syrup and upper fluid organic layer were formed. The lower layer was collected, solvent evaporated under nitrogen overnight followed by vacuum, 2 hours at 1 Torr to yield 15.3 grams of a tacky tan solid. $^1$H-NMR & $^{31}$P-NMR were run on this solid with an internal standard, trimethyl phosphate, to show a 50:50 ratio of DMVP:SVS derived groups.
The tacky tan solid was mixed with 30 grams of water and 45 grams of concentrated HCl (≈37%) to yield a milky white solution. This mixture was refluxed for 48 hours to yield a transparent solution with a slight brown color. The water and HCl were stripped from the solution on a roto-vap operating at 60° C. and 20 torr to a total volume of ≈20 mL. 100 additional mL of water was added to this remaining fraction and the stripping was repeated, then 200 mL of water was added, the sample was frozen and lyophilized to yield 11.8 g of tan solid. $^{31}$P-NMR showed a shift in the polymer beak from ≈37 to ≈32 ppm, while the $^1$H-NMR showed the disappearance of the peak polymer peak at ≈3.8 ppm that corresponded to the methyl ester peak. Analysis with an internal standard indicated a ratio of P containing groups to sulfur containing groups of approximately 47 to 53, and a weight activity of 82.4%

Example 8—Synthesis of Polymers Containing Phosphonate and Sulfonate Groups

A phosphonate monomer selected from the proton or sodium form of vinyl phosphonate, methyl vinyl phosphonate, styrene phosphonate, vinyl benzene phosphonate, (2-acrylamidoethyl)phosphonate, (2-(acryloyloxy)ethyl)phosphonate, (2-(methacryloyloxy)ethyl)phosphonate, (3-(methacryloyloxy)propyl)phosphonate, (2-(N-butylacrylamido)ethyl) phosphonate and (2-(vinyloxy)ethyl)phosphonate, and a sulfonate monomer selected from sodium or potassium form of vinyl sulfonate, methyl vinyl sulfonate, styrene sulfonate, vinyl benzene sulfonate, 2-acrylamido-2-methyl propane sulfonate, and 2-sulfopropyl acrylate, are added to a glass reaction vessel in a molar ratio of phosphonate:sulfonate of 10:90 to 90:10. Total solids is 10 to 50% by weight in water. System is degassed to remove oxygen and is stirred. A free radical initiator is added and the solution is heated or exposed to light to activate the initiator. Reaction is stopped when no additional consumption of monomer is detected. Resulting solution is purified by either solvent based extraction or dialysis to yield a purified product. Testing of purified product in PSPM shows reduced staining relative to the blank.

It is understood that the examples and embodiments described herein are for illustrative purposes only and that various modifications or changes in light thereof will be suggested to one skilled in the art without departing from its spirit and scope.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:
1. An oral care composition comprising a polymer comprising a first monomer comprising a phosphonate group and second monomer comprising an anionic group, wherein a ratio of the first monomer comprising the phosphonate group to the second monomer comprising the anionic group is in a range of from 66:34 to 20:80, wherein said polymer has the structure:

Formula 21

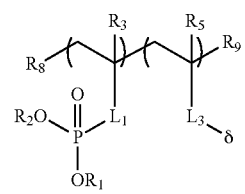

wherein:
R$_1$ is selected from the group consisting of —H, alkyl, alkanediyl-alkoxy, metal salt having Na, K, Ca, Mg, Mn, Zn, Fe, or Sn cation, and amine cation salt;
R$_2$ is selected from the group consisting of —H, alkyl, alkanediyl-alkoxy, metal salt having Na, K, Ca, Mg, Mn, Zn, Fe, or Sn cation, and amine cation salt;

$R_3$ is selected from the group consisting of —H and —$CH_3$;

$L_1$ is selected from the group consisting of a chemical bond, arenediyl, and a structure of Formula 3:

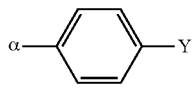

Formula 3 wherein:
- α is the site of attachment to the polymer backbone;
- β is the site of attachment to the phosphono-phosphate;
- X is selected from the group consisting of the structures in Formulas 4-10;

Formula 4

Formula 5

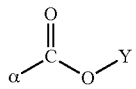

Formula 6

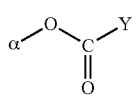

Formula 7

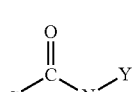

Formula 8

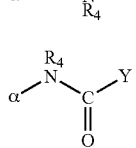

Formula 9

Formula 10 wherein:
- $R_4$ is selected from the group consisting of —H, $alkyl_{(C1-8)}$, phosphonoalkyl, and phosphono(phosphate)alkyl; and
- Y is selected from the group consisting of alkanediyl, alkoxydiyl, alkylaminodiyl and alkenediyl;

$R_5$ is selected from the group consisting of —H and —$CH_3$;

δ is the site of attachment to the anionic group;

$L_3$ is selected from a chemical bond, arenediyl, and a structure of Formula 13;

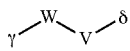

Formula 13 wherein:
- γ is the site of attachment to the polymer backbone;
- δ is the site of attachment to the anionic group;

W is selected from the structures in Formulas 14-20:

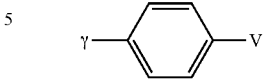

Formula 14

Formula 15

Formula 16

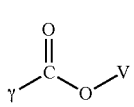

Formula 17

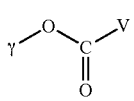

Formula 18

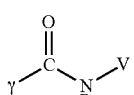

Formula 19

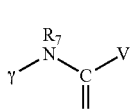

Formula 20 wherein:
- $R_7$ is selected from the group consisting of —H and $alky_{(C1-8)}$; and
- V is selected from the group consisting of alkanediyl, alkoxydiyl, alkylaminodiyl or alkenediyl;
- $R_8$ is a chemical group resulting from polymer initiation; and
- $R_9$ is a chemical group resulting chain termination, wherein the first monomer comprising the phosphonate group is a vinyl phosphonate monomer and the second monomer comprising the anionic group is a vinyl sulfonate monomer.

2. The oral care composition of claim 1 wherein $R_8$ is selected from the group consisting of the structures:

Formula 22

Formula 23

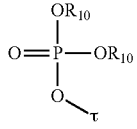

Formula 24

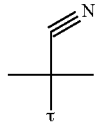

Formula 25

-continued

Formula 26

wherein:
R$_{10}$ is selected from the group consisting of —H, Na, K and amine cation salt;
τ is the site of attachment to polymer backbone; and
Q is the non-olefin residue of a monomer used in polymerization, wherein the oral care composition is a dentifrice composition.

3. The oral care composition of claim 2 wherein R$_9$ has the structure:

Formula 26

and Q has the structure:

Formula 27

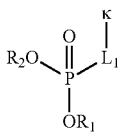

wherein κ denotes the site of attachment of Formula 27 to Formula 26.

4. The oral care composition of claim 2 wherein R$_9$ has the structure:

Formula 26

and Q has the structure:

Formula 28

wherein κ denotes the site of attachment of Formula 28 to Formula 26.

5. The oral care composition of claim 1 wherein R$_9$ is —H.

6. The oral care composition of claim 1 wherein R$_9$ is another polymer chain with a head to head attachment.

7. The oral care composition of claim 1 wherein said composition further comprises from about 5% to about 70%, by weight of the composition, of water.

8. The oral care composition of claim 1 wherein said composition further comprises from about 0.1% to about 11%, by weight of the composition, of a metal ion salt.

9. The oral care composition of claim 8 wherein said metal ion salt is stannous fluoride.

* * * * *